(12) United States Patent
Ivanov et al.

(10) Patent No.: US 11,958,251 B2
(45) Date of Patent: Apr. 16, 2024

(54) ADDITIVE MANUFACTURING SYSTEM WITH AT LEAST ONE ELECTRONIC NOSE

(71) Applicant: UT-Battelle, LLC, Oak Ridge, TN (US)

(72) Inventors: Ilia N. Ivanov, Knoxville, TN (US); Eric S. Muckley, San Diego, CA (US)

(73) Assignees: UT-BATTELLE, LLC, Oak Ridge, TN (US); UNIVERSITY OF TENNESSEE RESEARCH FOUNDATION, Knoxville, TN (US)

( * ) Notice: Subject to any disclaimer, the term of this patent is extended or adjusted under 35 U.S.C. 154(b) by 0 days.

(21) Appl. No.: 17/483,170

(22) Filed: Sep. 23, 2021

(65) Prior Publication Data
US 2022/0088876 A1 Mar. 24, 2022

Related U.S. Application Data

(60) Provisional application No. 63/081,962, filed on Sep. 23, 2020, provisional application No. 63/081,959, filed on Sep. 23, 2020.

(51) Int. Cl.
*B29C 64/386* (2017.01)
*A61B 5/00* (2006.01)
(Continued)

(52) U.S. Cl.
CPC .......... *B29C 64/386* (2017.08); *A61B 5/0004* (2013.01); *A61B 5/0816* (2013.01);
(Continued)

(58) Field of Classification Search
CPC ............ A61B 2562/046; A61B 5/0004; A61B 5/0816; A61B 5/082; A61B 5/6891;
(Continued)

(56) References Cited

U.S. PATENT DOCUMENTS 6,234,006 B1   5/2001   Sunshine et al.
8,499,613 B2   8/2013   Ziglioli et al.
(Continued)

FOREIGN PATENT DOCUMENTS

CN   113705100 A   11/2021
EP     2352024 A1    8/2011

OTHER PUBLICATIONS

Trill, H., "Diagnostic Technologies for Wound Monitoring", 2006, pp. 1-247.
(Continued)

*Primary Examiner* — Linda L Gray
(74) *Attorney, Agent, or Firm* — Scully, Scott, Murphy & Presser, P.C.

(57) ABSTRACT

An additive manufacturing system comprising at least one electronic nose (e-nose) is provided. The e-nose may comprise a housing and gas sensors. The housing may have an air channel. The active sensor portion of the sensors are positioned in the air channel. The housing may be mounted to an extruder head of an additive manufacturing device. The system may also comprise a processor. The processor may determine whether there is an abnormality in an additive manufacturing process based on one or more combinations of outputs from the gas sensors received during the additive manufacturing process input into a deployed machine learning model; and generate a report for the additive manufacturing process containing the determination.

18 Claims, 24 Drawing Sheets

(51) Int. Cl.

| | |
|---|---|
| *A61B 5/08* | (2006.01) |
| *B29C 64/364* | (2017.01) |
| *B33Y 30/00* | (2015.01) |
| *B33Y 50/00* | (2015.01) |
| *G01N 3/00* | (2006.01) |
| *G01N 21/25* | (2006.01) |
| *G01N 27/02* | (2006.01) |
| *G01N 33/00* | (2006.01) |
| *G01N 33/02* | (2006.01) |
| *G01N 33/497* | (2006.01) |
| *G05B 19/042* | (2006.01) |
| *G06N 3/00* | (2023.01) |
| *G06N 5/022* | (2023.01) |
| *G06N 5/04* | (2023.01) |
| *G06N 20/00* | (2019.01) |
| *G08B 21/18* | (2006.01) |
| *B33Y 10/00* | (2015.01) |

(52) U.S. Cl.
CPC .......... *A61B 5/6891* (2013.01); *B29C 64/364* (2017.08); *G01N 3/00* (2013.01); *G01N 21/25* (2013.01); *G01N 27/026* (2013.01); *G01N 33/0001* (2013.01); *G01N 33/0031* (2013.01); *G01N 33/0063* (2013.01); *G01N 33/0073* (2013.01); *G01N 33/02* (2013.01); *G01N 33/497* (2013.01); *G05B 19/042* (2013.01); *G06N 5/022* (2013.01); *G06N 5/04* (2013.01); *G06N 20/00* (2019.01); *G08B 21/18* (2013.01); *A61B 2562/046* (2013.01); *B33Y 10/00* (2014.12); *B33Y 30/00* (2014.12); *B33Y 50/00* (2014.12); *G01N 2203/0094* (2013.01); *G05B 2219/2614* (2013.01)

(58) Field of Classification Search
CPC ........ A61B 5/7267; B22F 10/18; B22F 10/85; B22F 12/90; B29C 64/106; B29C 64/364; B29C 64/386; B29C 64/393; G06N 20/00; G06N 20/10; G06N 20/20; G06N 3/008; G06N 5/01; G06N 5/022; G06N 5/04; G06N 7/01; G05B 19/042; G05B 2219/2614; G05B 23/024; B33Y 10/00; B33Y 30/00; B33Y 50/00; B33Y 50/02; G01N 21/25; G01N 2203/0094; G01N 27/026; G01N 3/00; G01N 33/0001; G01N 33/0031; G01N 33/0063; G01N 33/0073; G01N 33/02; G01N 33/497; G08B 13/19697; G08B 21/14; G08B 21/16; G08B 21/18; Y02P 10/25

See application file for complete search history.

(56) References Cited

U.S. PATENT DOCUMENTS

| | | | |
|---|---|---|---|
| 8,880,448 B2 | 11/2014 | Haddad et al. | |
| 9,201,035 B2 | 12/2015 | Chuang et al. | |
| 10,788,418 B2 | 9/2020 | Pi | |
| 2006/0191319 A1 | 8/2006 | Kurup | |
| 2011/0209524 A1 | 9/2011 | Ziglioli et al. | |
| 2012/0143804 A1 | 6/2012 | Haddad et al. | |
| 2013/0089642 A1* | 4/2013 | Lipson .................. | B33Y 10/00 426/115 |
| 2013/0105565 A1 | 5/2013 | Kamprath | |
| 2014/0221269 A1 | 8/2014 | Sobel et al. | |
| 2015/0000371 A1 | 1/2015 | Greene et al. | |
| 2015/0276700 A1 | 10/2015 | Goel et al. | |
| 2017/0293786 A1 | 10/2017 | Taylor et al. | |
| 2017/0363348 A1 | 12/2017 | Bogrash | |
| 2018/0018443 A1 | 1/2018 | Cho et al. | |
| 2019/0145947 A1 | 5/2019 | Oltyan et al. | |
| 2019/0272557 A1 | 9/2019 | Smith et al. | |
| 2019/0317118 A1 | 10/2019 | Khomami et al. | |
| 2020/0196793 A1 | 6/2020 | Ninomiya et al. | |
| 2020/0397188 A1 | 12/2020 | Tang et al. | |
| 2021/0072255 A1 | 3/2021 | Farokhzad et al. | |
| 2021/0172918 A1 | 6/2021 | Abdi et al. | |
| 2021/0199627 A1* | 7/2021 | Steen .................. | G01N 30/6095 |
| 2022/0274835 A1 | 9/2022 | Alvarez et al. | |

OTHER PUBLICATIONS

Lamagna, A. et al., "Performance of an e-nose in hops classification", Sensors and Actuators B, 2004, pp. 278-283, vol. 102.

Svechtarova, M. et al., "Sensor Devices Inspired by the Five Senses: A Review", Electroanalysis, 2016, pp. 1201-1241, vol. 28, No. 6.

Gardner, J. et al., "An Electronic Nose System to Diagnose Illness", Sensors and Actuators B: Chemical, 2000, pp. 19-24, vol. 70, No. 1-3.

Chatterjee, et al., "An E-Nose Made of Carbon Nanotube Based Quantum Resistive Sensors for the Detection of Eighteen Polar/Nonpolar Voc Biomarkers of Lung Cancer", Journal of Materials Chemistry B, 2013, pp. 4563-4575, vol. 1, No. 36.

Zhang, L. et al., "Classification of Multiple Indoor Air Contaminants by an Electronic Nose and a Hybrid Support Vector Machine", Sensors and Actuators B: Chemical, 2012, pp. 114-125, vol. 174.

Muckley, E. et al., "Low-Cost Scalable Quartz Crystal Microbalance Array for Environmental Sensing", SPIE Organic Photonics+ Electronics, International Society for Optics and Photonics, 2016, pp. 99440Y-1 to 99440Y-8, vol. 9944.

Aleixandre, M. et al., "Portable E-Nose to Classify Different Kinds of Wine", Sensors and Actuators B: Chemical, 2008, pp. 71-76, vol. 131, No. 1.

Dutta, R. et al., "Tea Quality Prediction Using a Tin Oxide-Based Electronic Nose: An Artificial Intelligence Approach", Sensors and Actuators B: Chemical, 2003, pp. 228-237, vol. 94, No. 2.

Le Maout, P. et al., "Polyaniline Nanocomposites Based Sensor Array for Breath Ammonia Analysis. Portable E-Nose Approach to Non-Invasive Diagnosis of Chronic Kidney Disease", Sensors and Actuators B: Chemical, 2018, pp. 616-626, vol. 274.

El Barbri, N. et al., "Building of a Metal Oxide Gas Sensor-Based Electronic Nose to Assess the Freshness of Sardines under Cold Storage", Sensors and Actuators B: Chemical, 2007, pp. 235-244, vol. 128, No. 1.

Dutta, R. et al., "Bacteria Classification Using Cyranose 320 Electronic Nose", Biomedical engineering online, 2002, pp. 1-7, vol. 1.

Apetrei, C. et al., "Combination of an E-Nose, an E-Tongue and an E-Eye for the Characterisation of Olive Oils with Different Degree of Bitterness", Analytica Chimica Acta, 2010, pp. 91-97, vol. 663, No. 1.

Vera, L. et al., "Characterization and Classification of the Aroma of Beer Samples by Means of an MS E-Nose and Chemometric Tools", Analytical and bioanalytical chemistry, 2011, pp. 2073-2081, vol. 399, No. 6.

Freund, M. et al., "A Chemically Diverse Conducting Polymer-Based "Electronic Nose"", Proceedings of the National Academy of Sciences, 1995, pp. 2652-2656, vol. 92, No. 7.

Lawless, H., "Descriptive Analysis of Complex Odors: Reality, Model or Illusion?", Food Quality and Preference, 1999, pp. 325-332, vol. 10, No. 4-5.

Nagle, H. et al., "The How and Why of Electronic Noses", IEEE spectrum, 1998, pp. 22-31, vol. 35, No. 9.

Lefever, E. et al., "In the Eye of the Beer-Holder. Lexical Descriptors of Aroma and Taste Sensations in Beer Reviews", HUSO 2017: The Third International Conference on Human and Social Analytics, 2017; pp. 25-29.

Tressl, R. et al., "Gas Chromatographic-Mass Spectrometric Investigation of Hop Aroma Constituents in Beer", J. Agric. Food Chem., 1978, pp. 1422-1426, vol. 26, No. 6.

(56) References Cited

OTHER PUBLICATIONS

Kishimoto, T. et al., "Comparison of the Odor-Active Compounds in Unhopped Beer and Beers Hopped with Different Hop Varieties", Journal of agricultural and food chemistry, 2006, pp. 8855-8861, vol. 54, No. 23.

Ghasemi-Varnamkhasti et al., "From Simple Classification Methods to Machine Learning for the Binary Discrimination of Beers Using Electronic Nose Data", Engineering in Agriculture, Environment and Food, 2015, pp. 44-51, vol. 8, No. 1.

Pornpanomchai, C. et al., "Beer Classification by Electronic Nose", 2008 International Conference on Wavelet Analysis and Pattern Recognition, IEEE, 2008; pp. 333-338.

Pedregosa, F. et al., "Scikit-Learn: Machine Learning in Python", Journal of Machine Learning Research, 2011, pp. 2825-2830.

Killeen, D. et al., "Vibrational Spectroscopy and Chemometrics for Rapid, Quantitative Analysis of Bitter Acids in Hops (*Humulus lupulus*)", Journal of agricultural and food chemistry, 2014, pp. 12521-12528, vol. 62, No. 52.

\* cited by examiner

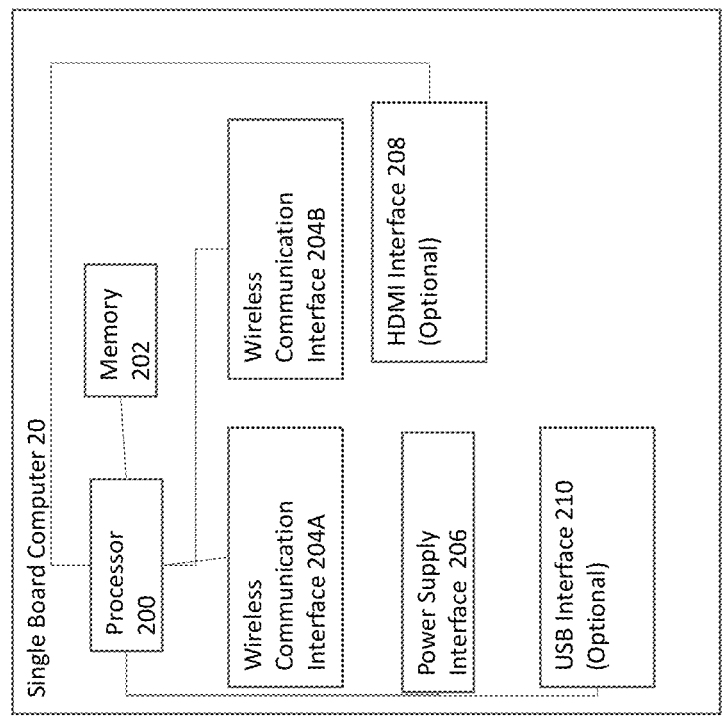

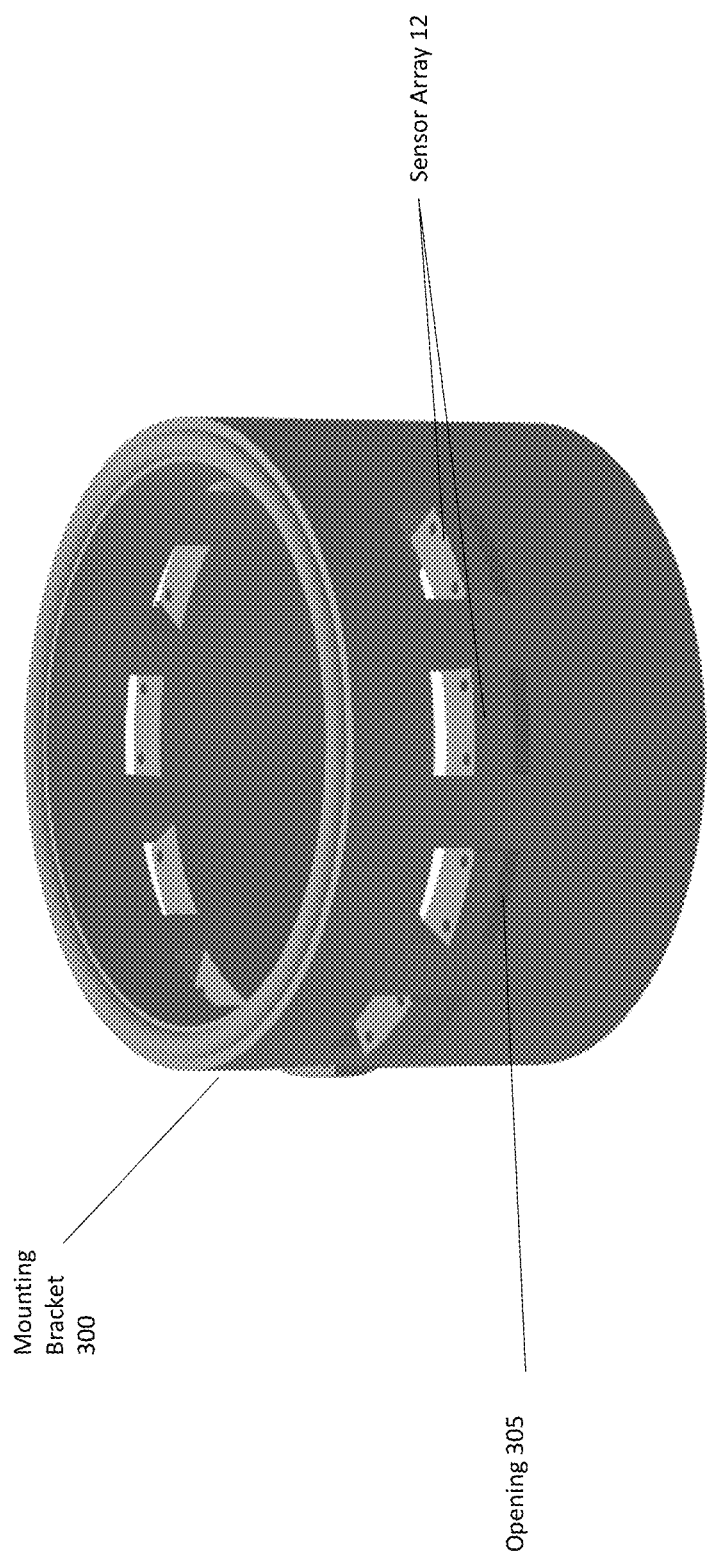

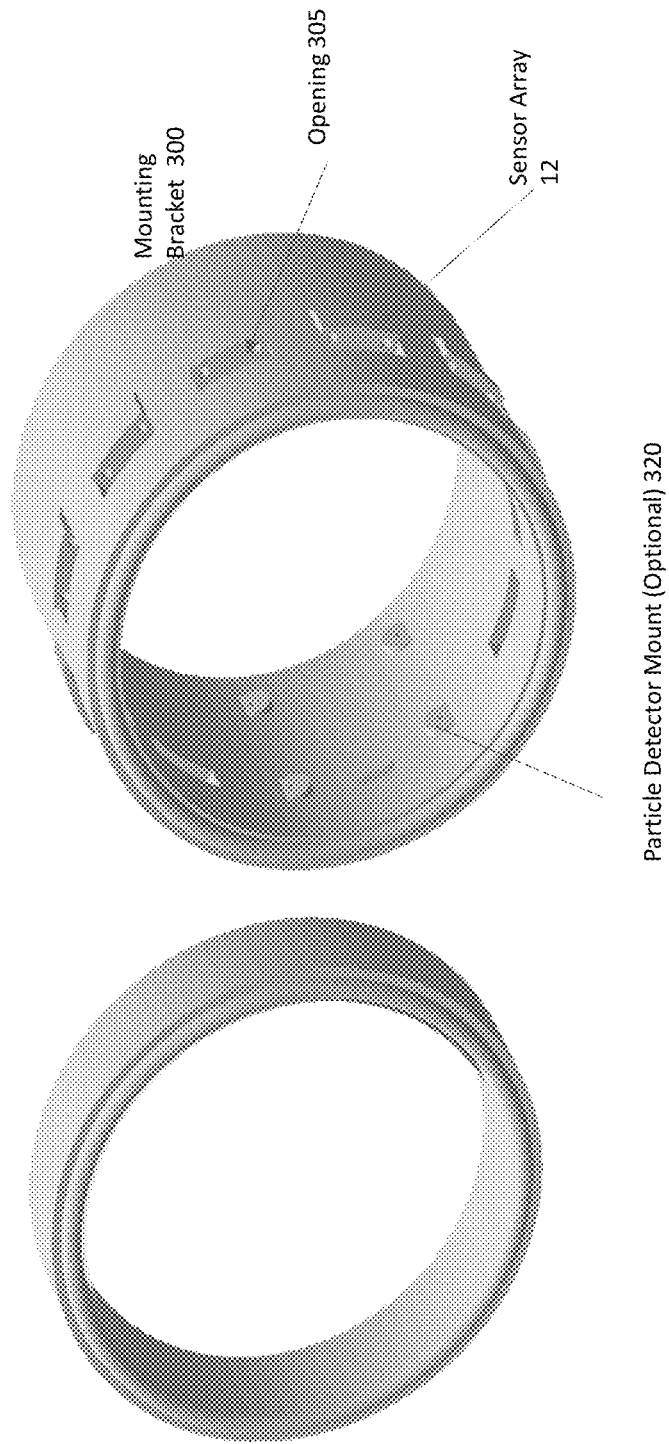

GUI
600

| Chemical Signature | TimeStamp | Position | Printing Conditions | Stopped | Other Information |
|---|---|---|---|---|---|
| | | | | | |
| | | | | | |

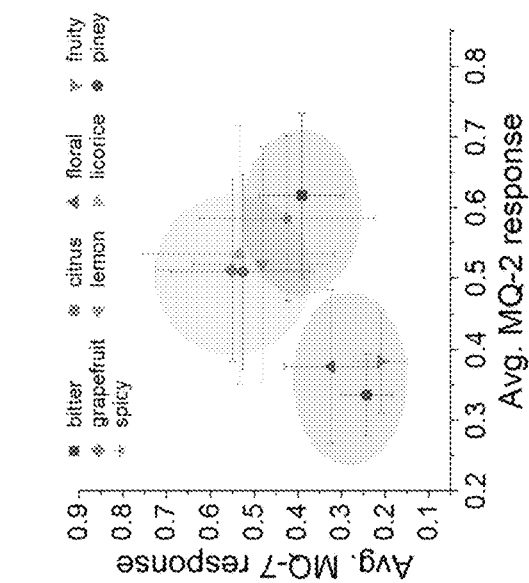
Fig. 19F
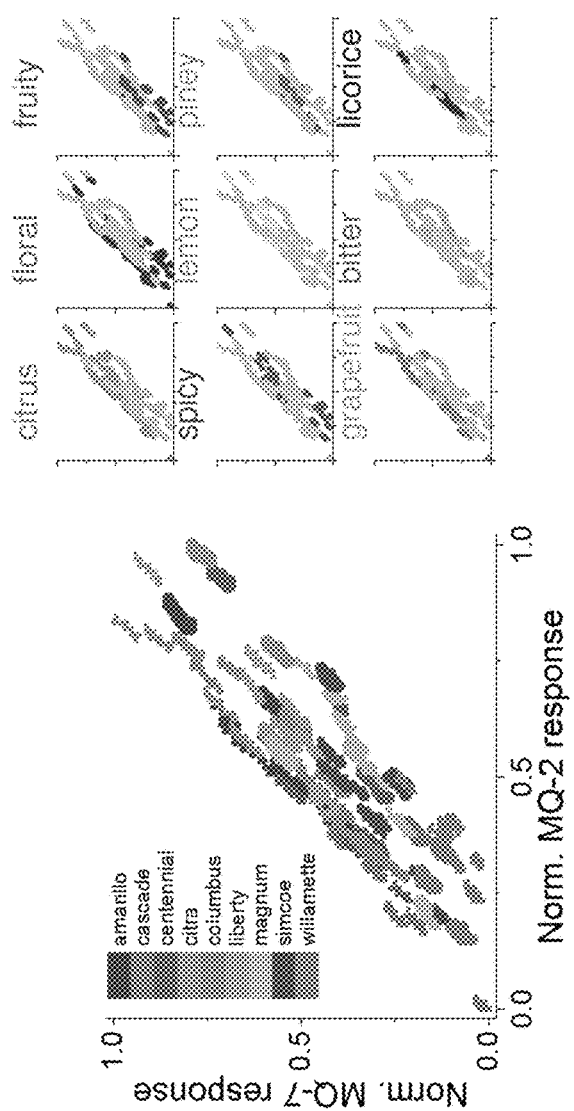
Fig. 19E
Fig. 19D

ADDITIVE MANUFACTURING SYSTEM WITH AT LEAST ONE ELECTRONIC NOSE

CROSS-REFERENCE TO RELATED APPLICATIONS

This application claims the benefit of and priority to U.S. Provisional Application Ser. No. 63/081,959 filed on Sep. 23, 2020 and U.S. Provisional Application Ser. No. 63/081,962 filed on Sep. 23, 2020, the entirety of which are incorporated by reference.

STATEMENT REGARDING FEDERALLY SPONSORED RESEARCH

The United States Government has rights in this invention pursuant to contract no. DE-AC05-00OR22725 between the United States Department of Energy and UT-Battelle, LLC.

FIELD OF THE DISCLOSURE

This disclosure relates to systems with at least one electronic nose with a plurality of gas sensors.

BACKGROUND

Aromas are present as an important characteristic of all natural and man-made products and their manufacturing, life of products providing unique distinct way of characterizing the owner and object. Aromas may be a sign of health, freshness of food or beverages (e.g., tea, coffee, etc.), quality of manufactured materials, as well as a sign of danger or imminent threat, as for example, the aroma may be from a toxic chemical. Therefore, correctly identifying, classifying and quantifying an aroma such that a person can understand it is important in various different applications.

SUMMARY

Accordingly, disclosed is a system for predicting one or more analytes based on outputs from a plurality of thin film gas sensors. The system may comprise an electronic nose (e-nose). The e-nose may comprise the thin film gas sensors and a first processor. The first processor may be configured to supply power to the plurality of thin film gas sensors to bias the sensors and receive output from each of the plurality of thin film gas sensors. The system may further comprise a second processor. The second processor may be configured to receive the output from each of the plurality of thin film gas sensors, generate randomly a first dataset for training and a second dataset for testing a plurality of models using the received output, train and test the plurality of models using one or more combinations of outputs from the plurality of thin film gas sensors, evaluate a prediction accuracy of each of the plurality of models using an evaluation parameter and select a model from among the plurality of models to deploy for detecting analytes based on a comparison of the evaluation parameter for each of the plurality of models. The second processor may also receive, an output of each of the plurality of thin film gas sensors caused by unknown one or more analytes; and predict, using the deployed model, the one or more analytes that causes the output.

The output from each of the plurality of thin film gas sensors may be in response to different analytes separately positioned near the plurality of thin film gas sensors, respectively, one at a time, and different combinations of analytes positioned near the plurality of thin film gas sensors, respectively, one at a time. The plurality of models may be generated using a plurality of different machine learning techniques. The training may be based on the first dataset and the testing based on the second dataset.

In some aspects, the second processor may be configured to predict, using the deployed model, the concentrations of the one or more analytes that causes the output. In some aspects, the deployed model for predicting the concentrations may be different from the deployed model for predicting the one or more analytes.

In some aspects, the second processor may be the same as the first processor.

Also disclosed is an additive manufacturing system. The system may comprise at least one electronic nose (e-nose). The e-nose may comprise a housing having openings on corresponding ends thereof to enable air flow, a plurality of thin film gas sensor; and a mount configured to mount the housing to an extruder head of an additive manufacturing device. The system may also further comprise a processor. The processor may be configured to supply power to the plurality of thin film gas sensors to bias the sensors, receive output from each of the plurality of thin film gas sensors, determine whether there is an abnormality in an additive manufacturing process manufacturing a product from one or more materials based on one or more combinations of output from the plurality of thin film gas sensors during the additive manufacturing process and a deployed machine learning model and generate a report for the additive manufacturing process containing the determination.

The housing may have an air channel for air to flow between the ends. The active sensor portion of each gas sensor is in the air channel to be exposed to the air flow.

In an aspect of the disclosure, the abnormality may be based on a predicted decomposition level determined from the output and the deployed machine learning model.

In an aspect of the disclosure, the additive manufacturing process may be stopped depending on the abnormality.

Also disclosed is a system for determining an age and/or quality of food or beverage. The system may comprise an electronic nose (e-nose). The e-nose may comprise a housing, a plurality of thin film gas sensors, at least one of an identification scanner, touch panel or image processor and a processor. The housing may have openings on corresponding ends thereof to enable air flow. The housing may have an air channel for air to flow between the ends. The active sensor portion of each gas sensor may be in the air channel to be exposed to the air flow. The identification scanner may be configured to read an identification code of a food or beverage. The touch panel may be configured to receive user input identifying the food or beverage. The image processor may be configured to analyze an acquired image of the food or beverage and identify the food or beverage. The processor may be configured to supply power to the plurality of thin film gas sensors to bias the sensors and receive output from each of the plurality of thin film gas sensors, predict the age and/or quality of the food or beverage based on one or more combinations of outputs from the plurality of thin film gas sensors and a deployed machine learning model and issue a notification of the determination.

In an aspect of the disclosure, the processor may be configured to determine that the food or beverage item or combination of items has expired when a predicted age correlates an age associated with a spoiled condition or is older than an age associated with spoiled condition.

In an aspect of the disclosure, the processor may be configured to determine the age of the food or beverage item, or combination of items based on a deployed machine learning model determined from images of the item or combination of items.

Also disclosed is a system for predicting one or more natural language descriptors associated with an aroma of an item. The system may comprise an electronic nose (e-nose). The e-nose may comprise a housing, a plurality of thin film has sensors and a processor. The housing may have openings on corresponding ends thereof to enable air flow. The housing may have an air channel for air to flow between ends. The active sensor portion of each gas sensor may be may be in the air channel to be exposed to the air flow. The processor may be configured to supply power to the plurality of thin film gas sensors to bias the sensors and receive output from each of the plurality of thin film gas sensors, calculate one or more ratios of the outputs of the plurality of thin film gas sensors, predict the one or more natural language descriptors using a logistic regression model using inputs of one or more outputs of the plurality of thin film gas sensors and the calculated one or more ratios; and output results of prediction.

In an aspect of the disclosure, the prediction may include a confidence.

In an aspect of the disclosure, the processor may further predict a percent depletion of the aroma.

BRIEF DESCRIPTION OF THE DRAWINGS

FIG. 2 is a diagram of a single board computer in accordance with aspects of the disclosure;

FIG. 3A and FIG. 3B are diagrams showing an example of a mounting bracket for mounting to an exhaust or duct in accordance with aspects of the disclosure;

FIG. 4 is a diagram in accordance with aspects of the disclosure;

FIG. 14 is a diagram of an example of a table for generating a quality report for an additive manufacturing process in accordance with aspects of the disclosure;

FIGS. 19A-19I are example graphs of different natural language descriptors and measured sensor responses from different hops in accordance with aspects of the disclosure, where FIGS. 19A, 19D and 19G show relationships between pairs of sensor outputs and the different hops, FIGS. 19B, 19E and FIG. 19H show the relationships between pairs of sensor outputs and the different natural language descriptors and FIGS. 19C, 19F and 19I shown clusters the relationships between pairs of sensor outputs and clusters of natural language descriptors;

DETAILED DESCRIPTION

Chemical Spillage Detection

Figure 1:
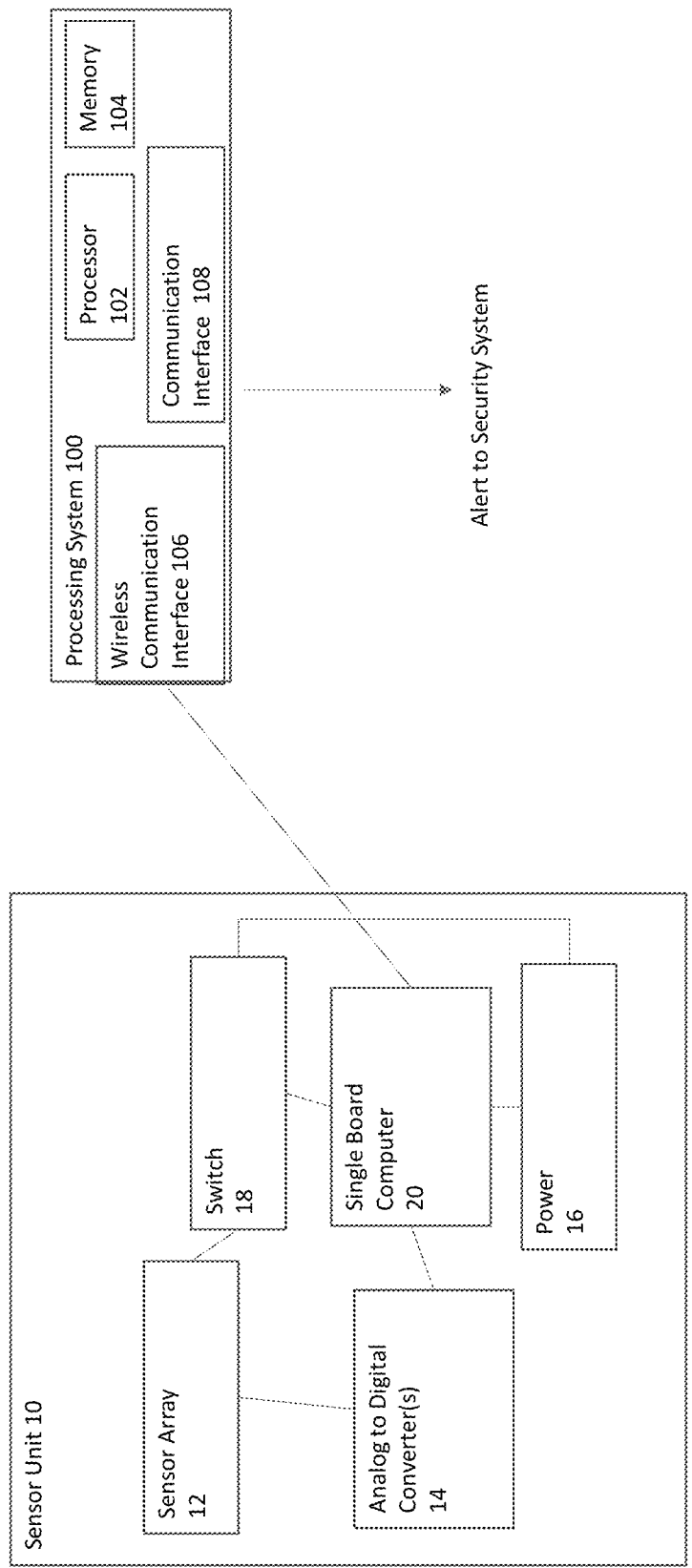
FIG. 1 is a diagram of a system in accordance with aspects of the disclosure.

FIG. 1 is diagram of a chemical detection and alert system 1 in accordance with aspects of the disclosure. The system 1 may be used to detect the type and/or concentration of chemicals and generate a warning or alert based on the detection. The system 1 may be used in any laboratory, factory or storage facility having chemicals.

The system 1 may comprise a sensor unit 10 having a sensor array 12. The sensor array may comprise a plurality of gas sensors. Each gas sensor has a measurable response in the presence of one or more gases, such as chemicals (also referred to herein an analytes). In some aspects of the disclosure, the measurable response is due to a change in resistance, which is measured by a voltage.

The number of the gas sensors in the sensor array 12 may be based on a particular application, such as a specific laboratory that only uses certain chemicals or a particular storage cabinet which is only used for certain chemicals. In some aspects of the disclosure, the gas sensors may be thin film gas sensors. For example, the sensors may be made of $SnO_2$. The nominal analyte selectivity of a sensor is designated by a sensor manufacturer. Each sensor may be tuned to be selectivity (sensitivity) to specific analytes. However, by combining the outputs as described herein (to generate a sensor pattern or output pattern), the sensor array 12 has extended capabilities and may be used to identify concentrations of analytes where each sensor is not specifically tuned to using one or more aspects of the disclosure such as through the training and testing of machine learning models and selection of one model from among a plurality of models (which will be described later in detail).

The sensors may be selected from MQ-2, MQ-4, MQ5 and MQ-7 sensors. For example, an MQ-2 gas sensor may be used for gas leakage detection such as $H_2$, LPG, $CH_4$, $C_3H_8$, CO, Alcohol, Smoke or Propane. An MQ-4 gas sensor may be used to detect analytes such as $CH_4$, alcohol, smoke. An MQ-5 gas sensor may be used to detect $H_2$, LPG, $CH_4$, CO, Alcohol. An MQ-7 gas sensor may be used to detect CO. In some aspects of the disclosure, as shown in FIG. 4, there may be nine gas sensors in the sensor array 12.

The gas sensors are not limited to the above, and other volatile organic compound sensors (VOX) sensors and inorganic compound sensors may be used including those on flexible substrate. The gas sensors may be positioned within an air flow in order to detect the analyte in the air flow.

In accordance with aspects of the disclosure, the system 1 may detect the concentration of the analyte in the air flow using one or more combinations of the outputs of the air sensors in the sensor array 12 (sensor patterns).

The sensor unit 10 may also comprise analog-digital converters 14 (ADC). The ADC 14 may be configured to convert the analog signals from the sensor array 12 to digital signals for further processing. In an aspect of the disclosure, each gas sensor may have its own ADC. The ADC 14 may be an integrated circuit as in part no. MCP3008. Each MCP3008 can convert up to eight analog signals into digital signals, respectively. Thus, when more than eight gas sensors (and other sensors) may be used, more than one MCP3008 may be needed. The ADC 14 may be attached to a power board. The power board may be connected to the sensor array 12 via a flexible connector (such as a 25 pin connector).

The sensor unit 10 may also comprise a single board computer 20. The single board computer 20 may be connected to the ADC 14 via the power board (via a flexible connector). The single board computer 20 may be a Raspberry PI (Raspberry Pi (Trading) Limited). The single board computer 20 causes power to be supplied to the sensor array 12 (as needed). Power may be supplied continuously or periodically based on user selection. The single board computer 20 also receives the digital signals from the ADC 14 and may store the digital signals locally. In an aspect of the disclosure, the data may be stored in some form of memory for post processing. For example, in some aspects, the data may be stored in a CSV format (and timestamped). Additionally, in some aspects of the disclosure, the single board computer 20 may calculate an average of individual outputs from the sensors and store the average. In some aspects, the single board computer 20 transmits the output from the sensors (digital version) to a server (processing system 100) for further processing. In other aspects, the single board computer 10 may transmit the calculated average of a selected number of outputs (digital version) from each sensor to the server (processing system 100).

The transmission may be via wireless communication. In other aspects, the transmission may be via a wired network.

FIG. 2 shows a block diagram of the single board computer 20 in accordance with aspects of the disclosure. The single board computer 20 may comprise a processor 200, a memory 202, wireless communication interfaces 204A/204B, a power supply interface 206, an HDMI interface 208 (optional) and one or more USB interfaces 210 (optional).

The processor 200 may be a microprocessor. The memory 202 may include Random Access Memory (RAM). In other aspects of the disclosure, the memory 202 may also include Read Only Memory (ROM). The ROM may store one or more programs such as a client program, when executed causes the processor 200 to execute the functionality described herein (such as, but not limited to, control of a switch based on user selection, calculating of averages based on user selection, periodically or continuation transmitting digital versions of outputs of the gas sensors to the processing system 100 (server)).

The wireless communication interfaces may be interfaces for WI-FI (Trademark) 204A and Bluetooth (Trademark) 204B. In an aspect of the disclosure, the single board computer 20 may communicate with the processing system 100 via the WI-FI interface 204A. In other aspects of the disclosure, information in the memory 202 may be transmitted to a local reader via the Bluetooth interface 204B. The local reader may be connected to the processing system 100 and upload the data. In other aspects of the disclosure, information in the memory 202 may be transmitted to a local reader via another wireless interface.

In other aspects of the disclosure, the single board computer 20 may comprise a wired network communication interface such as Ethernet. The single board computer 20 may communicate with the processing system 100 via the wired network (using an Ethernet cable).

The HDMI interface 208 or other display interface may be used to attach a display to view the sensor outputs.

The power supply interface may be a USB interface (such as USB-3). In other aspects of the disclosure, the power supply interface may be a barrel jack connector. In other aspects, the power supply interface may be connected to a power outlet or a standalone power source such as an external battery.

The gas sensors draw a significant amount of current to heat up (in order for sensing to be reversible). In accordance with aspects of the disclosure, the gas sensors may receive the power from a 5V, 4 A barrel jack (power 16). The barrel jack forms a shared power bus for the gas sensors and may be used to power the single board computer 20. This eliminates a need to have the USB interface 210 to power the single board computer 20. In an aspect of disclosure, the barrel jack may be soldered to the same board as the ADC 14. In other aspects of the disclosure, the power for the system 1 may be solar power and the sensing unit 10 may have a solar cell and be positioned to capture light.

In an aspect of the disclosure, the sensor unit 10 may also comprise a switch 18. The switch 18 may be a N-channel MOSFET. This switch 18 may be controlled by the single board computer 20 (processor 200) based on user selection (setting). Advantageously, by using the switch 18, electricity is not wasted when the gas sensors are not actively being used and needed. Not shown in FIG. 1, a rectifier diode and pull-down resistor may be connected to the N-channel MOSFET. The resistor maintains the MOSFET OFF by default. The rectifier diode prevents any back electromotive force (EMF) caused by the sensor array 12 (plurality of gas sensors).

Also not shown in FIG. 1, the sensor unit 10 may also comprise other sensors such as a humidity sensor, a pressure sensor and a temperature sensor (particle detector or dust sensor). These sensors may be used for calibration and adjustment of the output signals from the gas sensors, as needed.

These other sensors do not use a significant amount of power and therefore, may be directly connected to the single board computer 20.

Figure 5A:
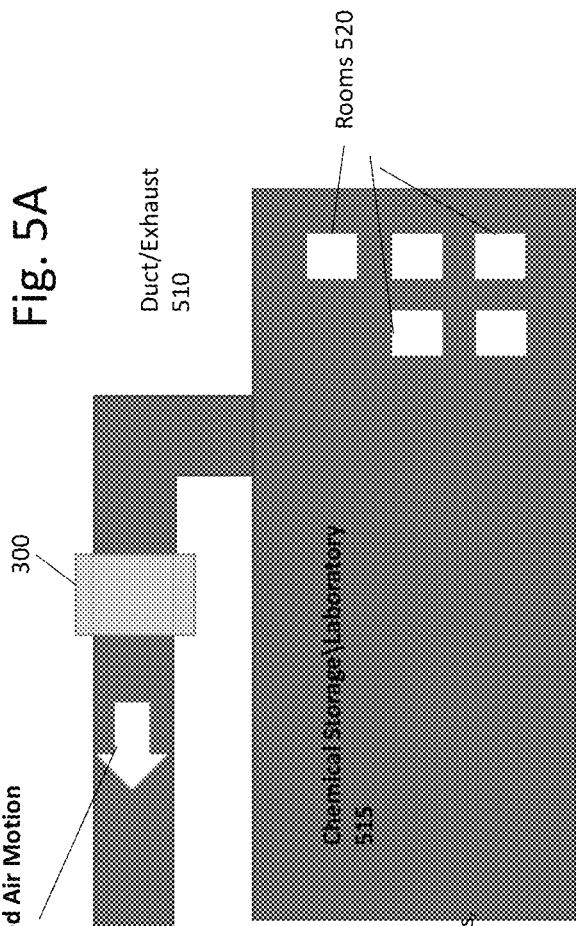
FIG. 5A is a diagram showing the mounting location for the sensor unit in accordance with aspects of the disclosure.
Figure 5B:
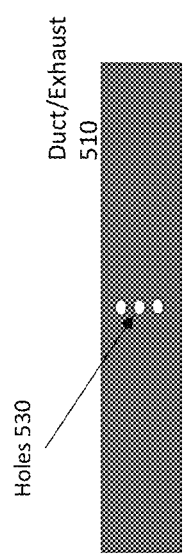
FIG. 5B shows openings or holes in the air flow passage in accordance with aspects of the disclosure and FIG. 5C shows a view of the mounting bracket in sections.

An active sensor portion (such as the active surface or sensor head) 525 of each sensor in the sensor array 12 is positioned in air flow passage. The air flow passage may be, but is not limited to, a hood, an exhaust, an air duct in a building such as a laboratory. In an aspect of the disclosure, the active sensor portion 525 of each sensor may be positioned in the air flow passage through a mounting bracket 300. The mounting bracket 300 may be attached to or connected to a duct, pipe, exhaust, or any path of an air flow in a controllable manner. The air flow passage may have corresponding openings or holes 530 as shown in FIG. 5B to receive the active sensor portion 525. The air flow passage may have different shapes such as circular, oval, rectangular. The bracket 300 may mimic the shape of the exterior of the air flow passage to assure leak free mounting of the active sensor portion.

FIGS. 3A and 3B depict different views of a mounting bracket 300. The mounting bracket 300 may be fabricated using additive manufacturing such as 3D printing. The dimensions may be based on the dimensions of the air flow path. While the mounting bracket 300 is shown in FIGS. 3A and 3B as tubular, as noted above, the bracket 300 may have other shapes.

Figure 5C:
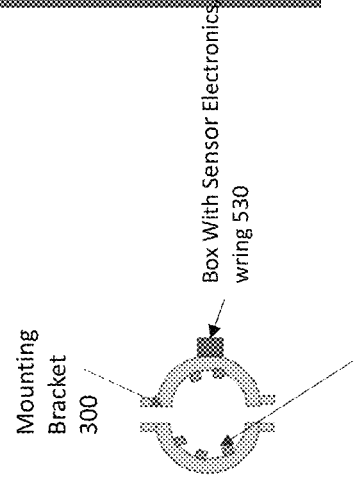

As shown in FIGS. 3A and 3B, mounting bracket 300 also has openings 305 one for each gas sensor. The active sensor portion 525 may be connected to its corresponding circuitry which may be in a box 530 via the opening in the bracket. The electronic circuitry of each sensor may be mounted on the exterior air flow passage and the bracket 300 exterior such as shown in FIG. 5C to protect it from potentially harsh environments inside the air flow passage which may lead to damage of electronic circuitry. The footprint of the active sensor portion 525 inside the air flow passage should be minimal to reduce formation of stagnation zones above the sensor and restriction of the air flow. In other aspects, instead of openings 305, the mounting bracket 300 may have recesses forming compartments for the sensor body, e.g., circuitry, such that the active sensor portion 525 may be inside the air flow passage when the mounting bracket 300 is attached to the air flow passage. While FIGS. 3A and 3B show the mounting bracket 300 as a complete tube, the bracket 300 may be formed from multiple parts as shown in FIG. 5C such that it may be clamped to the air flow passage.

In other aspects, instead of a mounting bracket 300, a part of the air flow passage may be replaced with an assembly. The assembly may have compartments or recesses such that the gas sensors may be positioned in the same to enable the active sensor portion 525 to face the air flow passage and be in the air flow. In other aspects, the assembly may have openings for each sensor and the sensors may be positioned in a respective opening such that the active sensor portion 525 may be positioned in the air flow. The assembly may be attached to the remaining portion of the air flow passage via welding or other known means of attachment.

In an aspect of the disclosure, the mounting bracket 300 may also include additional attachment points 320 for other sensors such as a particle detection mount. While in FIG. 3B, the particle sensor 400 may be attached to the inner surface of the bracket 300, in other aspects, the bracket may have an additional opening or recess (compartment) for the particle sensor 400. The opening or recess (compartment) may have a similar function, e.g., to hold the particle sensor 400 such that the active sensor portion (surface) is within the air flow passage (while certain circuitry is external).

In other aspects, the bracket 300 or assembly may have supports or projections 300A for mounting each sensor such as shown in FIG. 4.

In FIG. 4, nine gas sensors are mounted on projections 305A from the inner wall of the bracket 300. The particle detector 400 is attached to the mounting bracket 300. A power board with the jack and the ADC 14 is connected to the sensor array 12 using flexible connectors with pins (25 pin connector). The single board computer 20 is connected to the power board with a flexible connector.

As described above, the mounting bracket 300 is intended to be mounted in an air flow passage by fitting over a vent or exhaust dust 510 and attaching by an attachment means as described above. FIG. 5A illustrates an example of a mounting location for the mounting bracket 300 in a building such as a laboratory. In an aspect of the disclosure, the processing system 100 may be mounted to the outside of the vent or exhaust dust. In other aspects, the processing system 100 may also be mounted to a wall near the vent or exhaust dust 510. Additionally, the single board computer 20, ADC 14 and power 16 may be mounted to the outside of the vent or exhaust dust 510 and located on a wall near the same. FIG. 5A illustrates that the mounting bracket 300 is connected to a duct or an exhaust 510 for a laboratory (chemical storage). In this aspect of the disclosure, the air is moving via forced air 505 such as part of a ventilation system including an HVAC system. The air may be circulated via one or more fans.

Figure 9:
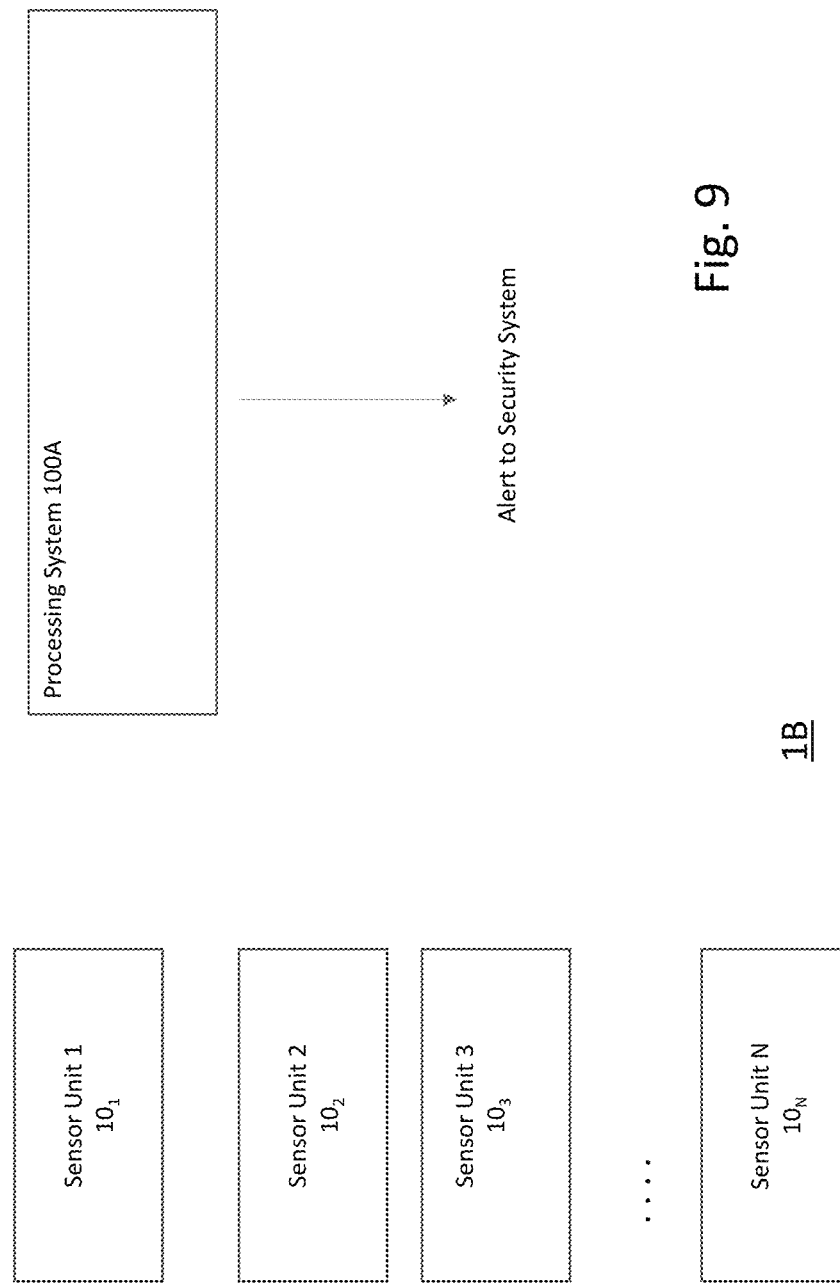
FIG. 9 is a diagram of another system in accordance with aspects of the disclosure.

In an aspect of the disclosure, the mounting bracket 300 may be in a central duct 510 that receives air flow from multiple rooms 520 such as shown in FIG. 5A. However, in other aspects of the disclosure, the mounting bracket 300 may be in an individual room duct or exhaust. In this aspect of the disclosure, multiple sensor units 10 may be deployed such as shown in FIG. 9.

Figure 6:
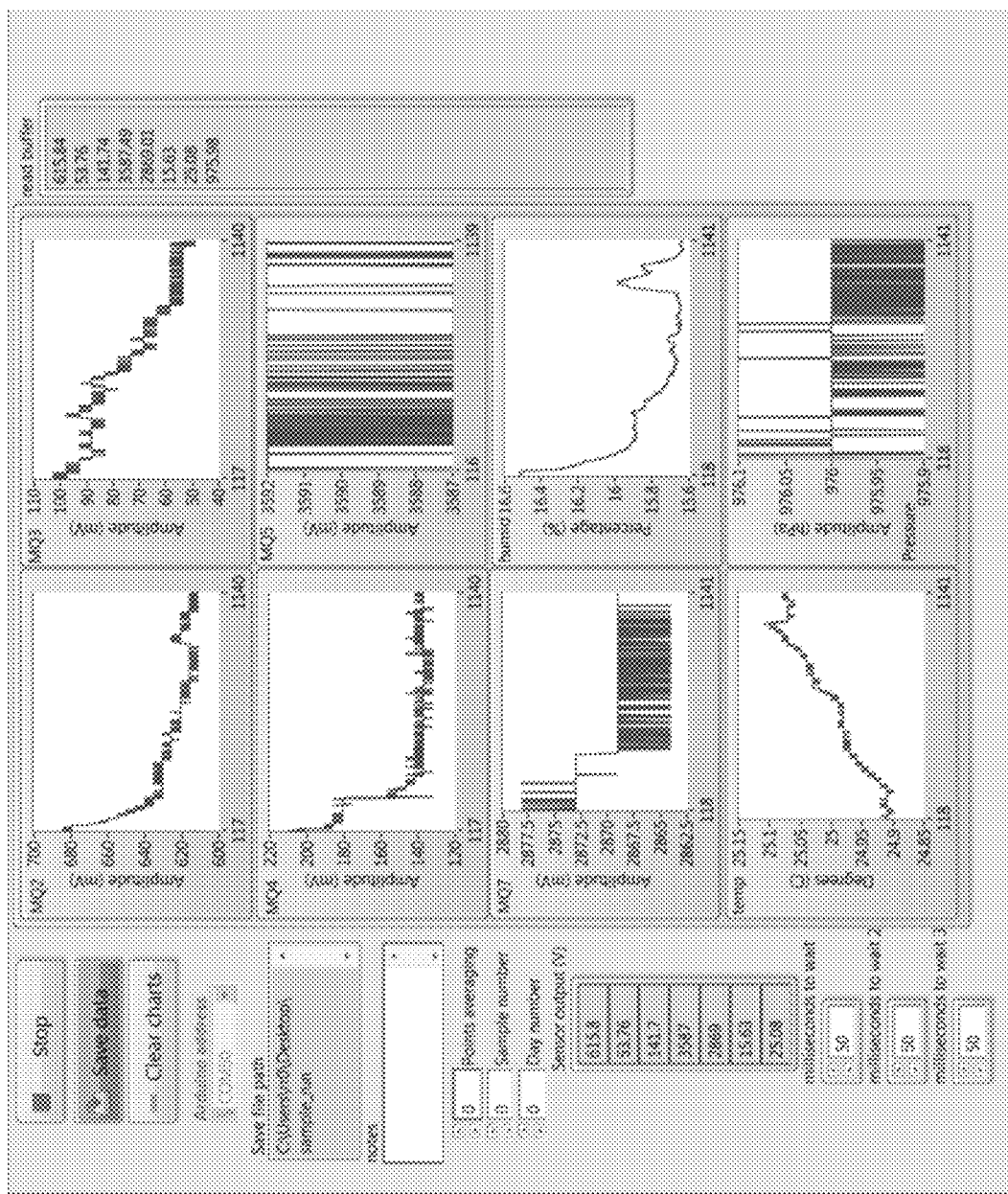
FIG. 6 is a diagram of an example of a graphical user interface in accordance with aspects of the disclosure.

FIG. 6 illustrates an example of a graphical user interface 600 (GUI) which may be used to select/set sensing parameters. The sensing parameters may include continuous, periodic or aperiodic. If periodic, the parameters may include frequency, such as each minute, 5 minutes, 10 minutes, 30 minutes, 1 hour . . . . In an aspect of the disclosure, the period may be the same for each day. Alternatively, the frequency may vary depending on the time of day or the day of the week. For example, during normal work hours, the period may be shorter than overnight. Additionally, the period may be shorter during the weekday than the weekend.

The GUI 600 may also be used to set whether averaging of sensor output may be used in the processing. For example, the user may set that the sensor output is averaged using a plurality of readings such as 2, 5, 10, 25 . . . etc. When averaging is set, the processor 200 may calculate the average of the different outputs (from the same gas sensor) prior to transmission to the processing system 100 (server).

In other aspects of the disclosure, the GUI 600 may be used to view the outputs from each gas sensor (and any other sensor). In an aspect of the disclosure, the single board computer 20 may transmit the sensor output to a device running the GUI 600. The GUI 600 may be executed on any device connectable to a network. For example, the device may be a personal computer, a mobile device such as a mobile phone, tablet, laptop, etc. In other aspects, the device may communicate with the processing system 100 and obtain the sensor output for display on the GUI 600 from the processing system 100.

Referring back to FIG. 1, the system 1 may further comprise a processing system 100. The processing system 100 may act as a server for the single board computer 20. The processing system 100 may comprise a processor 102, a memory 104, a wireless communication interface 106 and communication interface 108.

For example, the processor 102 may be a CPU. In other aspects, the processor 102 may be a microcontroller or microprocessor or any other processing hardware such as a FPGA. The processor may be configured to execute one or more programs stored in a memory 104 to execute the functionality described herein.

The memory 104 may be ROM and RAM. The memory may be any piece of hardware capable of temporarily or permanently storing data. The wireless communication interface 106 may be a WI-FI (trademark) interface. The wireless communication interface may communicate with the sensor unit 10 (single board computer 20). The communication may be bi-directional.

The communication interface 108 may be a wired communication interface such as Ethernet. The processing system 100 may communicate with another system via the communication interface 108. For example, the processing system 100 may communicate with a security system to provide an alert that a chemical has been spilled. The alert may include a time of the spillage, e.g., timestamp of the sensor output that indicated a spillage, the chemical (analyte) and concentration. The concentration and analyte being determined from one or more combinations of sensor outputs and a deployed machine learning model.

In an aspect of the disclosure, the processor 102 is configured to execute machine learning to create a model for concentrations of analyte. The model is trained and tested using a dataset. In an aspect of the disclosure, the model may be updated when a new analyte is added (e.g., training/testing repeated). The dataset may be stored in the memory 104 and in some aspects, in a CSV format.

Figure 7:
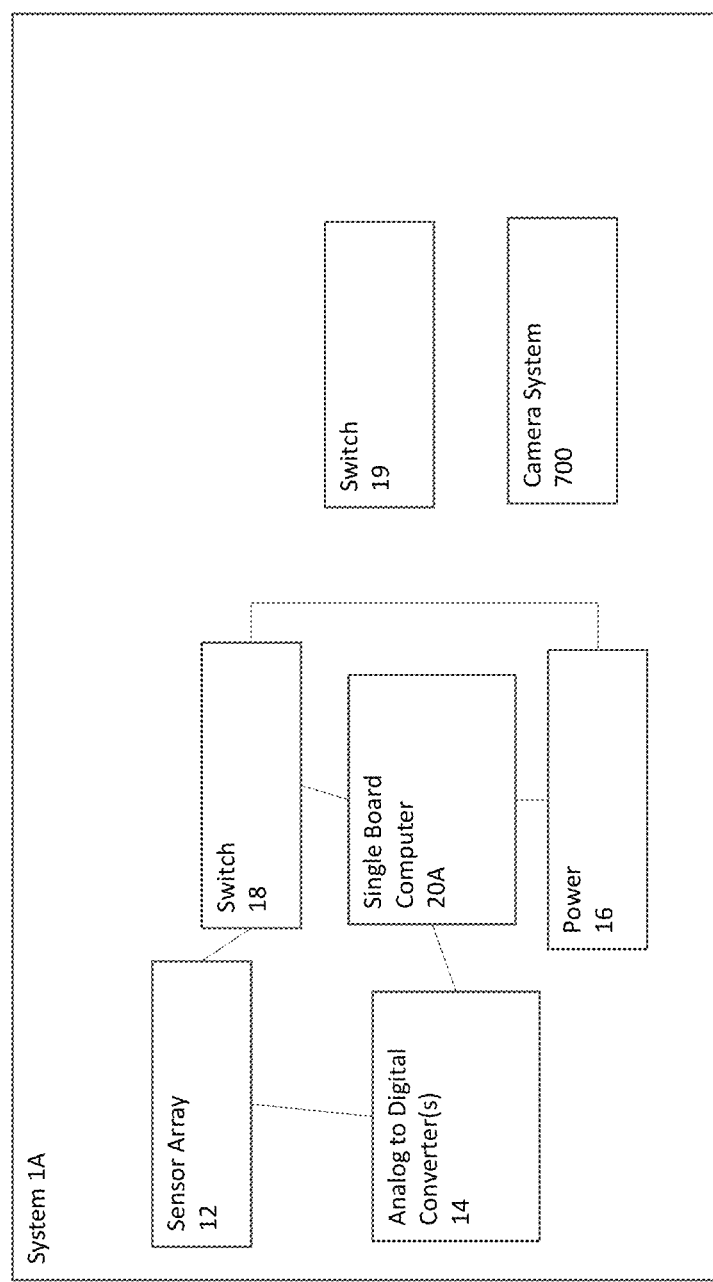
FIGS. 7 and 8 are diagrams of another system in accordance with aspects of the disclosure.
Figure 8:
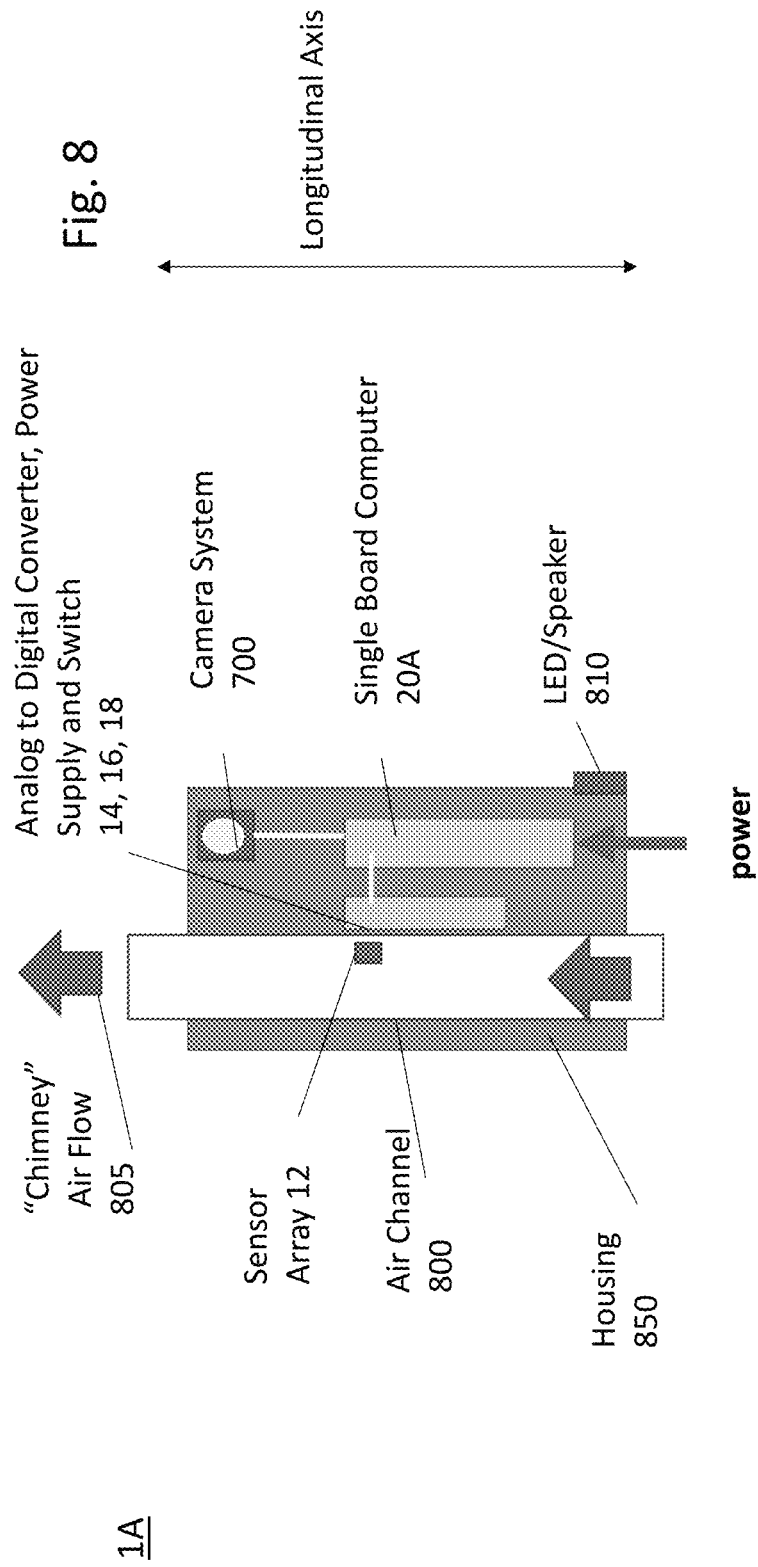

FIGS. 7 and 8 depict another system 1A in accordance with aspects of the disclosure. Instead of being mounted to a duct or exhaust (or hood), the system 1A may be portable and have a handle (not shown). In other aspects of the disclosure, the housing 850 of the system 1A may be mounted to a wall in a room or a wall of a chemical storage cabinet (or a rack). The housing 850 may be mounted to a wall using brackets or a railing system. In other aspects of the disclosure, the housing 850 may be mounted to a wall via an adhesive. The housing 850 is mounted in the orientation as shown in FIG. 8 such that the longitudinal axis is parallel to the direction of the air flow 805.

In an aspect of the disclosure, the system 1A may be placed on a base or stand such that the system 1A may to located on a desk or test bench, shelf, etc. The base or stand may be hollow in the center to allow air flow to enter the system 1A from the bottom.

In an aspect of the disclosure, the system 1A may be handheld and a handle may be attached to the housing 850 to enable a user to hold the system 1A. In an aspect of the disclosure, the system 1A may be mounted to a ceiling, where the ceiling has an opening or a vent.

The housing 850 has an opening on the bottom and a corresponding opening on the top. The opening allows air to flow into the system 1A from the bottom and leave the system 1A at the top (the direction of the air flow is shown in FIG. 8 with arrows). The system 1A may comprise a vertical air channel 800. The air channel 800 may be a pipe such as a PVC pipe. The shape of the opening where air flows to the air channel 800 may be round, oval rectangular or any other shape to match the shape of the air channel 800. As described above, a mounting bracket 300 or assembly may be used having a plurality of sensors attached or inserted such that the active sensor portion (surface) 525 of each sensor of sensor array 12 is exposed to the air flow (however the circuitry may be outside the air flow passage, e.g., air channel 800 such as contained in a box 530). The sensors which work at elevated temperatures may be mounted above sensors which operate at ambient temperatures to assure adequate air sampling inside the air flow passage (e.g., air channel 800). If more than one sensor in the sensor array 12 operates at high temperature (T>ambient), the position of such sensors may be distributed evenly around the air channel 800. In some aspects, the air channel 800 may have a plurality of recesses. When sensors having a flexible substrate used, the sensors may be mounted in recesses, such that the flexible substrate is flashed with inner part of the air channel 800 to reduce restriction to air flow. The sensors with electronic control boards (circuitry) may be detached from the electronic boards and mounted through small holes on the air channel 800 using ring mounting racket (for cylindrical pipe). In an aspect of the disclosure, electronic boards (circuitry) of the sensors may be assembled inside the environment protected box.

In other aspects of the disclosure, the air channel 800 may be fabricated via additive manufacturing. In other aspects, instead of a bracket 300, similar to described above, the air channel 800 may openings on the side which functions as an access holes for elements of sensor array 12 such that the active sensor portion 525 faces the air flow and is exposed to the air flow such the circuitry may be external to the air flow (mounted within the open or external to the air channel 800). Sensor access openings may be evenly distributed over the diameter. If more sensors are accommodated than can be integrated on the perimeter of the air channel 800, several air channels 800 may be implemented.

As in system 1, the sensor array 12 may comprise a plurality of gas sensors. The number of gas sensors in the sensor array 12 may depend on the application. In some aspects, where the system 1A is portable or wall mount in a particular room or storage cabinet, the number of gas sensors in the sensor array 12 may be less than the number where the gas sensors are located within the duct or exhaust. For example, in an aspect of the disclosure, the sensor array 12 may have four gas sensors. The system 1 may also have other sensors such as a particle detector (sensor).

In an aspect of the disclosure, since the gas sensors are heated such that the sensing is reversible, the heat of the gas sensors within the air channel 800 naturally induces movement of the air within the air channel 800 due to convention. Therefore, there is no need for an addition source to cause the air to move within the air channel 800 such as a fan to force air motion.

The system 1A may also comprise a power board having an ADC 14, external power 16 and one or switches 18. Similar to above, the gas sensors may receive the power from a 5V, 4 A barrel jack (power 16). The ADC 14 may be an integrated circuit as in part no. MCP3008. Each MCP3008 can convert up to eight analog signals into digital signals, respectively. The switches 18 may be MOSFETs. Each gas sensor may have its own switch, or one switch may be used for all of the gas sensors in the sensor array 12.

The system 1A may also comprise a single board computer 20A. In an aspect of the disclosure, the single board computer 20A may be a Coral Dev Board available from Google (Trademark), LLC. In accordance with this aspect of the disclosure, the single board computer 20A may execute training, testing and deployment of a machine learning model from among a plurality of models, and determine concentration based on aspects of the disclosure instead of the processing system 100. The Coral Dev Board has an on-board Edge TPI coprocessor that is capable of performing high speed ML. The single board computer 20A may receive power from an external power source such as via a USB-C connection. In other aspects, the single board computer 20A may receive power from the power board (5V, 4 A barrel jack).

The system 1A may further comprise a camera system 700. In an aspect of the disclosure, the camera system 700 may be configured to take still images and/or moving images. The single board computer 20A may comprise one or more video interfaces such as s HDMI 2.0 or FFC connectors. In an aspect of the disclosure, the system 1A may further comprises a switch 19 (such in FIG. 7) between the single board computer 20A and the camera system 700. The switch 19 may also be a MOSFET. The single board computer 20A may control the switch 19 based on a determination from one or more combinations of outputs from the gas sensor (e.g., based on determined concentration(s)). For example, when a determined concentration exceeds a threshold, the single board computer 20A may control the switch to close and power the camera system 700 and enable the camera system 700 to record still or moving images. This provides visual data of who is in the room when the concentration exceeds the threshold (evidence and tracing).

In an aspect of the disclosure, the system 1A may further comprise a notification device such as a speaker or light (LED) which emits a notification sound or light, respectively, when an event is determined, e.g., concentration exceeds a threshold. In some aspects of the disclosure, the system 1A may further comprise a display. The display may display a warning such as indicating the concentration detected, the analyte type and a timestamp of the time of detection (or time the output from gas sensors was received which triggered the determination). In an aspect of the disclosure, the display may be attached to or embedded in the housing 850. The display may be connected to a video connector. The speaker may be connected to an audio jack or terminal of the single board computer 20A. When a display is used, the single board computer 20A may cause the display to display the video or still image(s) taken by the camera system 700.

The single board computer 20A may also include similar components as described above and shown in FIG. 2, e.g., processor, memory, wireless communication interfaces and other communication interfaces. The memory may comprise programs for causes the single board computer 20A to execute the functionality described herein including a plurality of different machine learning algorithms (including for training, testing and deployment of a model), applying a trained/tested model to the gas sensor outputs, updating the models and deployment as needed. The memory may also comprise concentration thresholds used to determine whether to issue an alert or notification or activate the camera system 700. The memory may also include the output from the gas sensors, the determined concentrations, timestamps (associated with the outputs and concentrations) and video/still images obtained by the camera system 700.

In other aspects of the disclosure, instead of or in addition to the above notification device(s), the system 1A may transmit an alert to a security system or another device. The alert may comprise the analyte type (chemical), the concentration detected and a timestamp. In other aspects of the disclosure, the alert may comprise the video/still images combined with the analyte type, the concentration detected and a timestamp.

The single board computer 20A may interact with the GUI 600 in a similar manner as described above. For example, a user may input into the GUI 600 a frequency of activating the gas sensors (period) and reading averaged from the gas sensors. Additionally, the single board computer 20A may transmit the outputs from the gas sensors (and other sensors including particle detector) to the GUI 600 for display. The single board computer 20A may also transmit the alert (with or without video/still images) to the GUI 600. The GUI 600 may display the output from the sensors, the alert with determined concentration and the video/still images.

In other aspects of the disclosure, the camera system 700 may be omitted from the system 1A and the system 1A may be used to trigger and external camera system to record in the area where an event (high concentration is determined). The external camera system may be part of a buildings security system.

FIG. 9 illustrates another system 1B in accordance with aspects of the disclosure. In system 1B, there are a plurality of sensor units $10_{1-N}$ (collectively referenced as "10"). Each sensor unit 10 is in a particular area. For example, each sensor unit 10 may be located in/near a different room of a building. For example, the sensor unit 10 may be positioned in the duct associated with a room and obtain the air flow from the room. Each sensor unit 10 maintains its own log regarding outputs from the sensor array 12. Also, each sensor unit 10 (acting as a client) transmits the outputs (as directed) to the processing system 100A. The processing system 100A determines the concentration using a model (which was trained, tested and deployed). The processing system 100A may issue an alert to another system when the determined concentration is above a threshold. The other system may be a security system for the building. The processing system 100A maintains a log in memory of the outputs from the sensor array 12 from each sensor unit 10. Each sensor unit 10 is preset with the network address of the processing system 100A. In an aspect of the disclosure, the network address may be updated, as needed.

As described above, each sensor unit 10 transmits the outputs from the sensor array 12 to the processing system 100A (as needed, e.g., continuously or periodic). However, if a network connection fails, the sensor unit 10 may continue to collect the output from the sensor array 12 and store the same. The sensor unit 10 will repeatedly attempt to transmit the output and when connected, transmit output not previously transmitted. In this aspect of the disclosure, each sensor unit 10 may have a transmission flag indicating prior transmission (or not).

Figure 10:
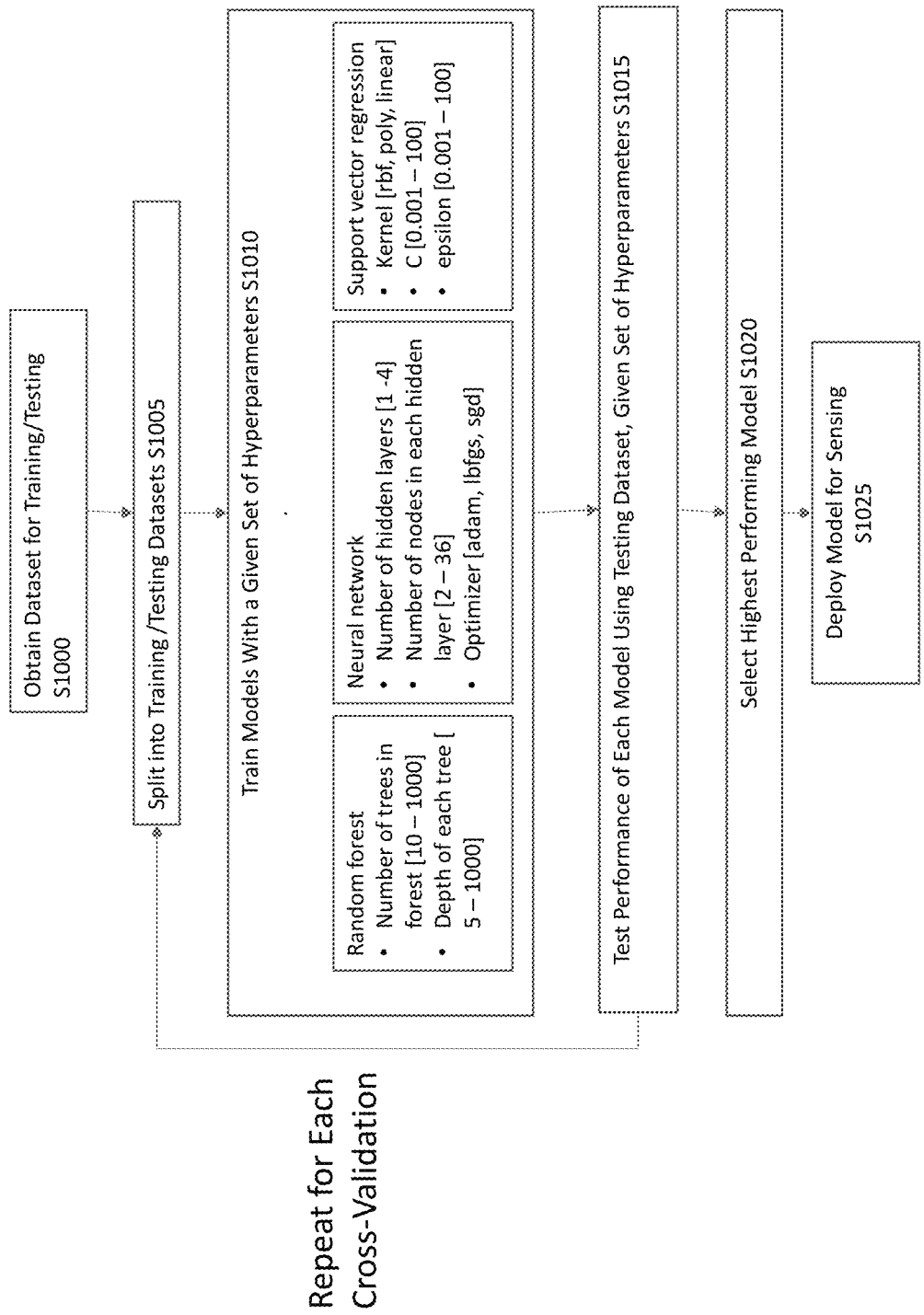
FIG. 10 is a flow chart illustrating a method for deploying a model(s) in accordance with aspects of the disclosure.

FIG. 10 is a flow chart illustrating a method for deploying a model(s) for determining concentration and type of analyte in accordance with aspects of the disclosure. At S1000, the dataset used for training and testing a plurality of models are obtained. The dataset used for training and testing may be different depending on whether the models are for identification of the type of analyte or for both identification and for determining a concentration. For example, in a case where the model is only for identification of the type of the chemical (and not for concentration), the dataset for each chemical and combinations of chemicals may only have sensor patterns for two points: a baseline where no chemical is in a test chamber and a second point where a specific amount of the chemical or combinations of chemicals are placed in the test chamber. On the other hand, in a case where the models are for determining both the type and the concentration, the dataset for each chemical and combinations of chemicals may have more points: a baseline where no chemical(s) are in the test chamber and a plurality of points at different known liquid volumes. The known liquid volumes may be converted into a concentration such as parts-per-million or a percentage using a vapor pressure and volume of the test chamber. The volume of the test chamber is known in advance.

The training/testing may be performed on different common solvents such as isopropanol, ethanol, methanol, acetone, etc . . . . The chemicals (and combinations thereof) used in the training and testing may be application specific. For example, where the system is deployed in a chemical storage cabinet, the training and testing may be done for each chemical and combination of chemicals in the chemical storage cabinet. The system (or just the sensor unit 10) may be positioned in a hood/exhaust or within the test chamber. Temperature and pressure sensors may be deployed in the environment for calibration and conversion. Vapor pressure is temperature dependent.

The acquisition time for each point may be predetermined, such as but not limited to 5 minutes. Each sensor output may be averaged. For the baseline measurement, no chemical was placed in or near the test chamber. The output from each sensor in the sensor array 12 may be averaged and recorded.

Afterwards, fixed amount of a first chemical may be injected onto a petri dish in the test chamber. This fixed amount of the first chemical may be where the vapor pressure in the syringe pump is saturated. The saturated vapor pressure is different for different analytes.

The fixed amount may be 100 ml. Other fixed amounts may be used. In a case where the training/testing is for a concentration, the vapor pressure and volume of the test chamber is used to determine the percentage or ppm associated with the liquid volume.

Information about the first chemical may be recorded into the system 1/1A/1B. The information may include information from NIOSH OSHA databases such as recommended exposure limits, lethal dose, immediate danger limits, flash point, autoignition temperature, explosive limits, coefficients for Antoine equation for calculating the vapor pressure for the chemical. This information may be used to determine the thresholds for alerts and autogeneration of instructions to responders with information on safety protocols related to said response.

The sensor array 12 may be exposed to the analyte (first chemical) for the same period of time, e.g., 5 minutes, and the outputs from each gas sensor may be averaged and recorded.

This process may be repeated for each single chemical used in the training/testing. However, between each data point, the sensor array 12 may be equilibrated to atmospheric conditions (baseline) until the response is stable. Once the data is collected for each single chemical, data may be collected for all potential combinations of the chemicals. For example, if there are four chemicals used for training and testing: A, B, C, D, the data may be collected for A, B, C, D, AB, AC, AD, ABC, ABD, BC, BD, BCD, CD, ACD, ABCD. Where combinations are used, the liquids of the different chemicals, may be separately injected into separate petri dishes.

When the training and testing is to deploy a model for concentration, in addition to obtaining the sensor output for the baseline and the fixed amount described above, data is acquired for multiple liquid volumes in between. For example, a calibration line may be created for each sensor in the sensor array 12. The calibration line may be a linear line between the baseline and the sensor output for the fixed amount described above. Another data point may be acquired between the baseline and the fixed amount (such as mid-way). For example, 50 ml of the first chemical may be used. Using the calibration line, an estimated sensor output may be determined. The sensor array 12 is exposed to the chemical (first chemical) for the same period of time, e.g., 5 minutes (after equilibrium), using the 50 ml injected into the petri dish in the test chamber (third point) and the outputs from each gas sensor may be averaged and recorded. Once again, the liquid volume may be converted into a percentage or ppm (concentration).

The difference between the measured output and the expected output may be determined. When there is a difference, it means that the response may be non-linear. When the response is non-linear, additional volumes of the chemical near the previous volume may be obtained for training/testing. In an aspect of the disclosure, when the error is less than the background, additional data points may not be further acquired, e.g., enough data has been acquired for training and testing models.

The calibration lines for each sensor may be updated with the measured output from the respective gas sensor. The calibration line may now be non-linear (curve). Additional data may be obtained in a similar manner for each single chemical, e.g., identify a new volume of the chemical, estimate the gas sensor(s) response, obtain the actual output and determine the distance. The new volume of the chemical for training/testing may be half of the previous amount. Additionally, as noted above, the new volumes may be based on the magnitude of the difference between the estimate response and the actual response. When the magnitude is larger than the difference from other estimated/actual responses, the next liquid volume may be closer to liquid volume with the larger difference.

The above process may be repeated for each single chemical, until the difference is less than a target amount.

The calibration lines (curves) for each sensor in the array 12 may be used to determine which sensors show the highest sensitivity to the chemical.

Once data points are collected for each single chemical (separately) at different liquid volumes, data points may be collected for different chemical combinations (at different combinations of liquid volumes). For example, when there are two chemicals (A and B), the liquid volume of A may be maintained at a specific volume and the liquid volume of B changes. Afterwards, the liquid volume of B may be maintained at a specific volume and the liquid volume of A is changed.

After the dataset is acquired (all of the data points are recorded), the processor 102 or single board computer 20A, splits the data into a training set and a testing set at S1005. In an aspect of the disclosure, the processor 102 or single board computer 20A uses 5-fold random cross-validation to split the dataset. For example, the model testing may be accomplished using the 5-fold cross-validation, where X % of the dataset is randomly selected to be used for training, and the remaining Y % of the dataset is used for testing. This process is performed for each model type and each combination of hyperparameters, and repeated 5 times so that a different training dataset is selected each time.

A S1010, a plurality of machine learning (ML) models may be trained using different combinations of hyperparameters using the training set split in S1005. The plurality of ML models includes models from different ML techniques include random forest, neural networks and support vector regression algorithms. The sets of hyperparameters may be randomly selected. For example, the hyperparameters for random forest include number of trees in the forest and depth of each tree. The hyperparameters for a neural network include number of hidden layers, number of nodes within each hidden layer, and an optimizer. The hyperparameters for the support vector regression algorithm include Kernel, C, and epsilon. The number of ML models trained (and tested) may be application specific or a user parameter. For example, 10000 different models/given hyperparameter sets may be trained. FIG. 10 shows an example of the bounds of the hyperparameters that may be used in the training. Different combinations of the gas sensor outputs may be evaluated in the training. For example, ratios of the gas sensor outputs may be used in the training. In addition, the individual outputs were also used as inputs to the ML models.

In some aspects, only the gas sensor outputs that had a high sensitivity may be used in the training. In some aspects of the disclosure, models may be trained to reach a predetermined percentage accuracy. For example, the predetermined percentage may be 95%. In some aspects, where the model is for both type and concentration, the model may be trained until the accuracy of both exceed 95%. In other aspects, different models may be trained for the type and concentration. If a model does not exceed the predetermined percentage, additional data may be acquired for different combinations of concentrations or types (more data points).

At S1015, the trained models may be tested using the testing set from S1005 (data from each cross-validation split). In an aspect of the disclosure, the performance of each model may be determined using a parameter such as root mean square error (RMSE). RMSE was determined based on the actual type/concentration and the predicted type and concentration using each model.

At S1020, the processor 102 or single board computer 20A selected the highest performing model from among the plurality of ML models trained and tested. For example, the processor 102 or single board computer 20A, compares the RMSE from each model and selects the model with the smallest RMSE. This model is subsequently used for sensing at S1025. For example, the model with a given hyperparameter configuration which performs the best at predicting the testing dataset on average over all the cross-validation splits may be selected to be deployed. The selected model is stored in memory S1025.

In an aspect of the disclosure, different models may be selected for the identification of the type and concentration for different chemicals or combinations. For example, one model may have the best RMSE for concentrations from Benzene and Ethanol while another model may have the best RMSE for isopropanol and acetone. Therefore, in accordance with aspects of the disclosure, different models may be used depending on the application. Furthermore. one model may have the best RMSE for identifying a type of chemical and a second model may be the best RMSE for determining concentration.

Figure 11:
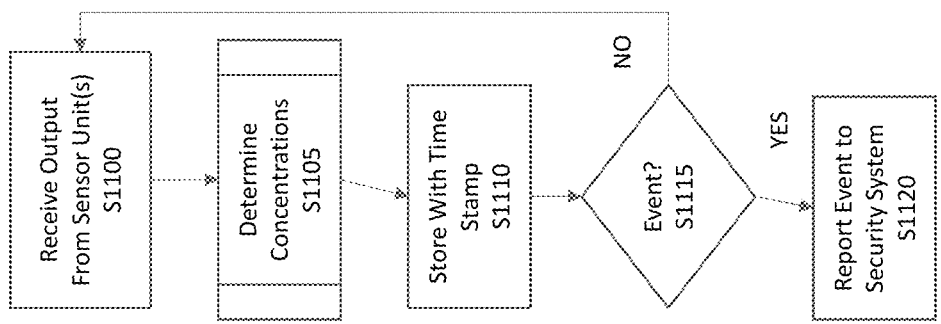
FIG. 11 is a flow chart illustrating a method in accordance with aspects of the disclosure.

FIG. 11 is a flow chart illustrating a method in accordance with aspects of the disclosure. In this aspect of the disclosure, the method is executed by the processing system 100/100A. At S1100, the processor 102 receives the outputs from the gas sensors from the sensor unit(s) 10 (such as via wireless communication). In some aspects of the disclosure, the outputs may be an average of a plurality of consecutive outputs (digital values) in time. The received data may be contained in a communication packet. The packet may have a header indicating the source of the packet (and destination). The received output from the gas sensors may also include an identifier identifying the specific gas sensor associated with the output.

At S1105, the processor 102 determines the concentrations of the analytes (and type) using the deployed model(s). In an aspect of the disclosure, the processor 102 retrieves the deployed models from the memory 104. In a case where there are multiple sensor units 10, there may be different deployed models for different sensor units. As described above, different models may be customized for different applications (chemical groups). For example, a building may have multiple rooms and each room may store or have different chemical(s) or combinations of chemicals. The different chemical(s) or combinations may lead to a different model deployed based on the deployment criterion. Therefore, the processor 102 may retrieve the deployed model(s) for the specific sensor unit 10 (based on the identifier in the source in the header).

Based on the deployed model(s) and the received gas sensor output (pattern), the processor 102 may calculate the parameters used in the deployed model(s). For example, if the deployed model relies on one or more ratios of the gas sensor outputs, the processor 102 calculates the one or more ratios. Also, if the deployed model relies on a multiplication, addition, subtraction (weighted or unweighted), the processor 102 makes the appropriate calculation(s) needed for the model. After making the appropriate calculations, the processor 102 applies the model(s) to the calculated values to obtain the type(s) (classification) and concentration(s).

At S1110, the processor 102 stores the determinations and a time stamp in the memory 104 as an entry. For example, the processor 102 stores the determined type(s) and concentration(s) with the time stamp in the memory 104 in a CSV format.

At S1115, the processor 102 determines whether an event has occurred. For example, the processor 102 may determine whether a chemical has been spilled in a room (or there is a leakage in a gas line or a storage bottle was not fully closed). In an aspect of the disclosure, this determination may be based on a comparison with a threshold. The threshold may be stored in the memory 104 as described above. In some aspects, different thresholds may be used for different chemicals (analytes). For example, chemicals that are more dangerous or harmful, may have a lower threshold. In some aspects, different thresholds may be used for the same chemical, e.g., recommended exposure limit, lethal dose, immediate danger limit, explosive limits etc.

For each type and concentration determined, the processor 102 may compare the concentration determined with the concentration threshold. When the processor 102 determines that the determined concentration exceeds the concentration threshold ("Y" at S1115), the processor 102 may issue an alert to another system such as a security system of the building at S1120. As described above, the alert may include the type and concentration detected (and the location). Different thresholds may have different warnings.

In other aspects, instead of using a preset concentration threshold, the processor 102 may determine that an event has occurred by comparing consecutive determined concentrations. Since the processor 102 stores the determined types and concentrations with a time stamp, the processor 102 may calculate a change in concentration for a particular chemical (analyte). The processor 102 may determine that an event has occurred when there is a change in concentration for the type between the consecutive times. In other aspects, the determination may be based on whether the change is higher than a threshold. In other aspects, the determination may use multiple consecutive concentration determinations and calculate a derivative or second derivative of the change.

The above method may be repeated for each sensor unit 10 in the system 1B (if there are multiple sensor units. In the case of multiple sensor units 10, the processor 102 may determine the location of the event based on the identifier of the sensor unit 10. Multiple sensor units 10 may be in the same room and the location of the event within the same room may also be identified based on the responses from each sensor unit 10 (e.g., different hoods in the same room).

The above method was described with respect to the processing system 100/100A (and processor therein) executing the features, however, in other aspects of the disclosure, as described with respect to FIGS. 7 and 8, there does not need to be a separate processing system remote (client/server configuration) and the single board computer 20A controls the gas sensors (causes power to be suppled, obtains the outputs, trains, tests, deploys the model(s) and determines the type(s) and concentration(s).

Figure 12:
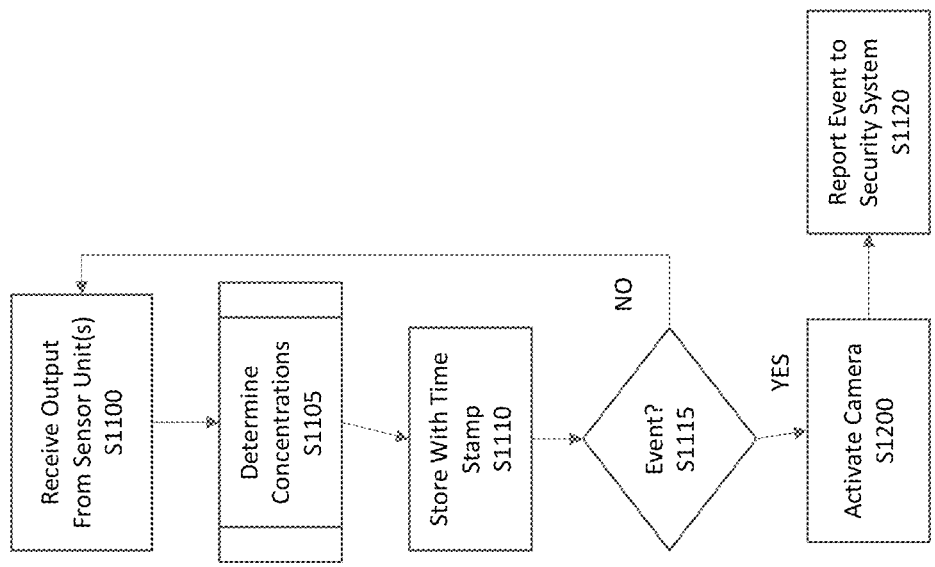
FIG. 12 is a flow chart illustrating another method in accordance with aspects of the disclosure.
Figure 13:
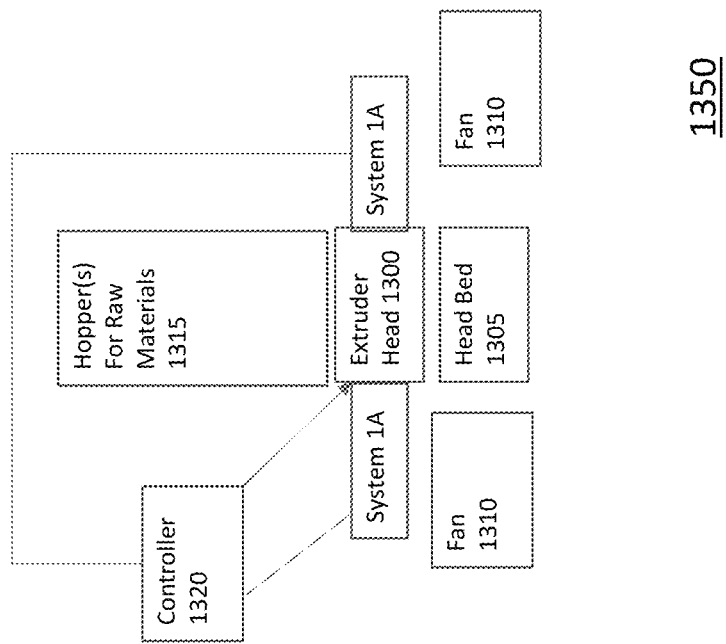
FIG. 13 is a block diagram of another system in accordance with aspects of the disclosure.

FIG. 12 is a flow chart illustrating another method in accordance with aspects of the disclosure. In this aspect of the disclosure, the method is executed by the processing system 100/100A. In this method, when an event is detected at S1115, the processor 102 may cause a camera system to activate at S1200. The camera system may be a standalone camera in a room or a camera which is part of a security system of a building.

In an aspect of the disclosure, where the single board computer 20A is executing the features in FIG. 12, the single board computer 20A may activate the local camera system 700 via a switch 19. In an aspect of the disclosure, the single board computer 20A may superposed a warning or indicator on the video or still images obtained from the local camera system 700. Additionally, the combined video/image with the warning may be transmitted to the security system.

Since the system 1A may be portable or positioned on a base, the system 1A may also be used for detecting abnormal compositions (type and concentrations) in a person's breathing. In this aspect of the disclosure, the system 1A may be trained and tested by obtaining a dataset of a person breathing near the system 1A (air channel 800) (person specific training). An event may be determined when there is a change in the compositions over time. In this aspect of the disclosure, the system 1A may transmit an alert to (1) the person; and (2) healthcare provider (doctor). In an aspect of the disclosure, the contact information for persons such as phone number, email address etc., may be registered into the memory in advance and the alert may be transmitted using the contact information.

In an aspect of the disclosure, the alerts may be transmitted based on the magnitude of change or concentrations. For example, a slight change may be alerted to a person whereas a large change or high concentration may be alerted to the healthcare provider.

Additive Manufacturing

In other aspects of the disclosure, the sensor systems described herein (such as the system 1A depicted in FIG. 7) may be used in an additive manufacturing system 1350. However, in some aspects, the camera system 700 may be omitted. The sensor system(s) may be used to determine whether there is a defect in a product made using an additive manufacturing process. Additive manufacturing makes three-dimensional objects from one or more materials. The materials may include polymers, metals and composite materials.

The polymer may be a thermoplastic resin, thermosetting resin or an elastomer. The thermoplastic resin may be polystyrene, polycarbonate, acrylic resin, etc . . . . The thermosetting resin may be epoxy, polyurethane, polyester, polyimide, polydimethylsiloxane (PDMS). The elastomer may be ethylene-propylene rubber, a polybutadiene rubber, a styrene-butadiene rubber, a chloroprene rubber, or a styrene-butadiene-styrene block copolymer. The product or object may contain more than one polymer.

The material(s) may be heated to certain temperatures using a flow rate (speed in which the materials are feed to the extruder head 1300) and manufactured on a head bed 1305. In some aspects, the extruder head 1300 may have a laser (such as for metal powder consolidation). A controller 1320 controls the temperature of the extruder head 1300 (heater or laser power) and the flow rate of the materials from the hopper(s) 1315.

Decomposition or changing the structure of material(s) leads to formation of defects in the manufactured object. "Object" and "Product" are used interchangeably herein. These defects, depending on the area(s) they occur may lead to the failure of the object in operation or use. However, during the additive manufacturing, decomposition may be unpredictable and randomly occurring.

In accordance with aspects of the disclosure, the gas sensors in the sensor array 12 provides information on the gas phases released from the material(s) used in the additive manufacturing process. For example, during metal additive manufacturing, the gas phase may contain metal oxide (partial or fully oxidized), particles and by-products of reaction of metal vapor with inert gas(es) or other gas(es). The gas phase in polymer additive manufacturing may include polymer and information regarding degradation of products. As such, in accordance with aspects of the disclosure, the machine learning model(s) may be trained/tested and deployed to detect signatures indicating a change in quality of gas phases (environment around the extruder head 1300) to determine a defect in the manufacturing process and may stop printing, as needed.

In accordance with aspects of the disclosure, one or more sensor systems 1A may be mounted to the extruder head 1300. In an aspect of the disclosure, the systems 1A may be mounted using a mounting bracket. In an aspect of the disclosure, this same mounting bracket may be used to mount the extruder head to the remaining parts of the additive manufacturing device. The description herein refers to system 1A however other of the described systems may be used. For example, one sensor system 1A may be mounted on the left side of the extruder head 1300 and another sensor system 1A may be mounted on the right side of the extruder head 1300. Since the extruder head 1300 may move both rightward and leftward in the additive manufacturing process, the gas phase may be received by the air channel in one of the systems 1A irrespective of the direction of movement of the head 1300. In some aspects of the disclosure, one or more fans 1310 may be used to direct the airflow to the air channel in the system 1A. In some aspects, since the gas sensors may be temperature sensitive, the housing 850 of the system 1A may be mounted via an insulator to thermally isolate the gas sensors from the heat used in the additive manufacturing process. For example, thermal tape may be used.

In an aspect of the disclosure, the controller 1320 may be in communication with the system 1A. The communication may be wireless. The controller 1320 may transmit the manufacturing temperature (laser power), flow rate and coordinate of the printing (x, y, z) to the system 1A (to the single board computer 20A). In other aspects, the same processor (controller) may be used to control all aspects of the additive manufacturing process and defect determination in accordance with aspects of the disclosure.

In an aspect of the disclosure, the model for determining a defect in the product may be trained, tested and deployed in a similar method as described above in FIG. 10. However, the dataset used for training and testing may be acquired differently.

The dataset for training and testing of a plurality of models for polymers and composite materials may be obtained heating the same to a plurality of different temperatures (and using a plurality of different flow rates). In an aspect of the disclosure, to avoid any damage to the extruder head 1300, the dataset may be obtained using a hot plate positioned below the system 1A (gas sensor array 12). The hot plate may be positioned within the housing of the additive manufacturing device, such as a printer. The hot plate may be controlled to heat a polymer and composite material to a desired temperature(s). For example, as a baseline value, the temperature may be the glass transition temperature of the material. Different polymers have different glass transition temperatures and thus may have a different baseline. The dataset may be generated for multiple different temperatures above the glass transition temperature. The highest temperature in the temperature range for acquisition of the dataset may be +100 C above the glass transition temperature. The highest temperature may be set based on the expected additive manufacturing temperature (even under an abnormal condition). For example, typically even under an abnormal condition, the additive manufacturing temperature is unlikely to exceed the glass transition temperature by more than 100 C.

The first data point in the dataset may be obtained by heating a sample of a particular polymer to the glass transition temperature Tg for that particular polymer. Tg is a known temperature for a polymer. The outputs of each of the gas sensors in the sensor array 12 may be recorded. The recorded values may be an average of a plurality of consecutive sensor values. For example, the sensor readings may be taken over a 1 minute period or 2 minute period. Additionally, the recording may be started after stabilization occurred in the temperature. Background readings (noise adjustment) may be used to normalize or account for typical gases in the environment, e.g., obtain sensor output prior to placing the polymer in the hot plate and heating.

Once the first data point is obtained, the second data point in the dataset may be obtained by heating a sample of the particular polymer to Tg+100 (maximum) after waiting for the gas sensors in the sensor array 12 to return to the output without any heating or gas sensing (e.g., background normal values). The sensor output of each sensor in the sensor array 12 may be averaged and recorded. A calibration line may be created for each gas sensor in the sensor array 12. The calibration line may be a linear line between the baseline (Tg) and the gas sensor output for the Tg+100 C described above. Another data point may be acquired between the baseline (Tg) and the Tg+100 C (such as Tg+50 C). Using the calibration line, an estimated sensor output may be determined. A sample of the polymer may be heated to Tg+50 and the sensor array 12 is exposed for the same period of time, e.g., 1 or 2 minutes (after equilibrium), and the outputs from each sensor may be averaged and recorded.

The difference between the measured output and the expected output may be determined. When there is a difference, it means that the response may be non-linear. When the response is non-linear, additional data from heating temperatures near the previous temperature may be obtained for training/testing.

The calibration lines for each sensor may be updated with the measured output from the respective sensor. The calibration line may now be non-linear (curve). Additional data may be obtained in a similar manner for each heating temperature of the same polymer, e.g., estimate the sensor(s) response, obtain the actual output and determine the distance. In some aspect, the new heating temperature for training/testing may be half of the previous amount. Additionally, as noted above, the new heating temperature may be based on the magnitude of the difference between the estimate response and the actual response. When the magnitude is larger than the difference from other estimated verses actual response, the next heating temperature may be closer to temperature with the larger difference.

The above process may be repeated until the difference is less than a target amount.

In other aspects, the dataset may be obtained starting from Tg and heating a sample in increments of 10 degrees steps until a maximum is reached (Tg+100 C). In other aspects, the dataset may be obtained starting from Tg and heating a sample in increments of 1-degree steps until a maximum is reached (Tg+100 C). In this aspect, the dataset may have 10-100 different patterns of sensor outputs from the sensor array 12. In other aspects, the temperature may be maintained, but the flow rate changed to obtain data points at different flow rates.

The above process may be repeated for each polymer or composite material expected to be used in the additive manufacturing process. In other aspects of the disclosure, when other types of additive manufacturing processes are used (such as using a laser), the dataset may be obtained for different laser powers instead of different heating temperatures.

An abnormal condition may be detected during the manufacturing when the actual sensor response corresponds to a predicted temperature (from the deployed model) higher than the temperature received from the controller 1320 (target temperature used).

In other aspects of the disclosure, the dataset may include measurements and data from different modalities of measurements. The different modalities may also measure the gas phase or solid phase such as mass spectroscopy, Fourier-transform infrared spectroscopy, thermal gravimetric analysis, and Raman spectroscopy. These modalities of measurements may be conducted simultaneously with the gas sensing via the sensor array 12. For example, a FT-IR spectrometer from Bruker VERTEX series may be used for the FTIR spectroscopy. A Thermogravimetric Analyzer available from TA Instruments such as Discovery TGA 55, TGA 550 or TGA 5500 may be used for the thermal gravimetric analysis. An InVia confocal Ramon microscopy may be used for the Raman spectroscopy. While these modalities of measurements may be used for training/testing and deployment of a model (correlation), once the model is deployed, only the gas sensor output from the sensor array 12 may be used as the input for predicting the temperature and decomposition as the other modalities may be costly. These other modes of measurement may be used at each temperature in the dataset (acquisition temperature). The modes may be used for detection of decomposition of the product as a function of temperature.

Additionally, mechanical testing/analysis may be obtained and included in the dataset. The mechanical testing may be acquired from printing an object using the extruder head 1300. While the dataset may include gas sensing and spectroscopy measurements from Tg–Tg+100 C, the mechanical testing may only occur at a subset of the range, e.g., Tg–Tg+20 C to avoid damaging the extruder head 1300. The mechanical testing may include manufacturing one or more predetermined shaped objects using the polymer (or composite material) (for each polymer/composite material) at different temperatures.

The mechanical analysis at each temperature may include closeness to target shape (warping), adhesion and strength such as Young's modulus. The mechanical analysis may identify key areas of weakness (in the product), e.g., locations, which may be critical to the overall design of the product. For example, when there is an abnormal printing within a product (not on the surface), the defect may not impact the shape such as warping, however, when the abnormal printing is at the surface, it may impact the shape. For example, by overheating a polymer, the surface may be curved and not be able to be formed with sharp angles (corners). This may be a critical defect and cause rejection of a product. Additionally, if the abnormal printing is on a base of a product, e.g., weight bearing, and causes the strength of the object to be reduced, the base may not be strong enough to hold the weight of other layers of the product, causing failure of the product.

In an aspect of the disclosure, the results of the mechanical analysis may be manually entered into the dataset for each temperature that the analysis was performed. The entry may include the type of failure, e.g., issue such as warping or strength and positioned of the failure and whether the failure is a key or critical position and tolerances. This information may be used to determine whether to stop the additive manufacturing process prior to finishing the product.

Once the dataset is generated for each polymer or composite material (and metals), the dataset may be divided into sets for training and testing in a similar manner as described above.

In some aspects of the disclosure, different models may be deployed for different polymers or composite materials. Therefore, the dataset for the same polymer or composite material may be used to generate the training and testing sets.

In other aspects, the same model may be deployed for the different polymers and composite materials.

As described above, a plurality of machine learning (ML) models may be trained using different combinations of hyperparameters using the training set. The plurality of ML models includes models from different ML techniques include random forest, neural networks and support vector regression algorithms. The sets of hyperparameters may be randomly selected. For example, the hyperparameters for random forest include number of trees in the forest and depth of each tree. The hyperparameters for a neural network include number of hidden layers, number of nodes within each hidden layer, and an optimizer, The hyperparameters for the support vector regression algorithm include Kernel, C, and epsilon.

The number of ML models trained (and tested) may be application specific or a user parameter. For example, 10000 different models/hyperparameter sets may be trained where FIG. 10 shows an example of the bounds of the hyperparameters that may be used.

Different combinations of the gas sensor outputs may be evaluated in the training. For example, ratios of the gas sensor outputs may be used in the training. In addition, the individual outputs of the sensors in the sensor array 12 were also inputs to the models.

In some aspects, only the sensor outputs that had a high sensitivity may be used in the training. In some aspects of the disclosure, models may be trained to reach a predetermined percentage accuracy. For example, the predetermined percentage may be 95%. If a model does not exceed the predetermined percentage, additional data may be acquired for different temperatures.

The trained models may be tested using the testing set (data from each cross-validation split). In an aspect of the disclosure, the performance of each model may be determined using a parameter such as root mean square error (RMSE). RMSE was determined based on the target temperature and the predicted temperature using the model.

The highest performing model from among the plurality of ML models trained and tested is selected for deployment. For example, the single board computer 20A, compares the RMSE from each model and selects the model with the smallest RMSE. This model is subsequently used for sensing. The selected model is stored in memory.

In accordance with aspects of the disclosure, the single board computer 20A may maintain a table 1400 of information associated with the additive manufacturing process of a product such as shown in FIG. 14. The information in the table 1400 may be used to generate a report (digital passport) for the product. The report may be generated for each product or object manufactured.

In an aspect of the disclosure, the table 1400 may include information received from the controller 1320 such as the x, y, z position of the extruder head 1300 (pixel being printed), printing conditions (such as temperature or laser power, a flow rate, type of material, e.g., what the polymer, metal or composite material is), time the printing started, and other information such as manufacturer of the material, batch number of the material, etc. The table 1400 may also include information determined by the single board computer 20A such as the chemical signature (gas pattern), whether an abnormal condition has occurred (such as predicted temperature using model verses target temperature of printing is different), a timestamp of received gas sensor output and whether printing (manufacturing) of the product is stopped.

The report (digital passport) may be used for post-failure analysis (if the manufacturing is allowed to continue) and the product ultimately fails in use. The post-failure analysis may include determining whether there is a design issue with the part or a one-time failure. In other aspects of the disclosure, the reports (digital passports) may be used to determine if there is an error or failure in the printer itself. For example, if multiple reports indicate an abnormality in the manufacturing process for multiple different products (of the same or different design) within the period of time), this may indicate that the printer needs to be recalibrated or repaired. Additionally, if the reports indicate an abnormality in the manufacturing process only for the same product (in the same location), this may indicate a flaw in the design of the product.

Figure 15:
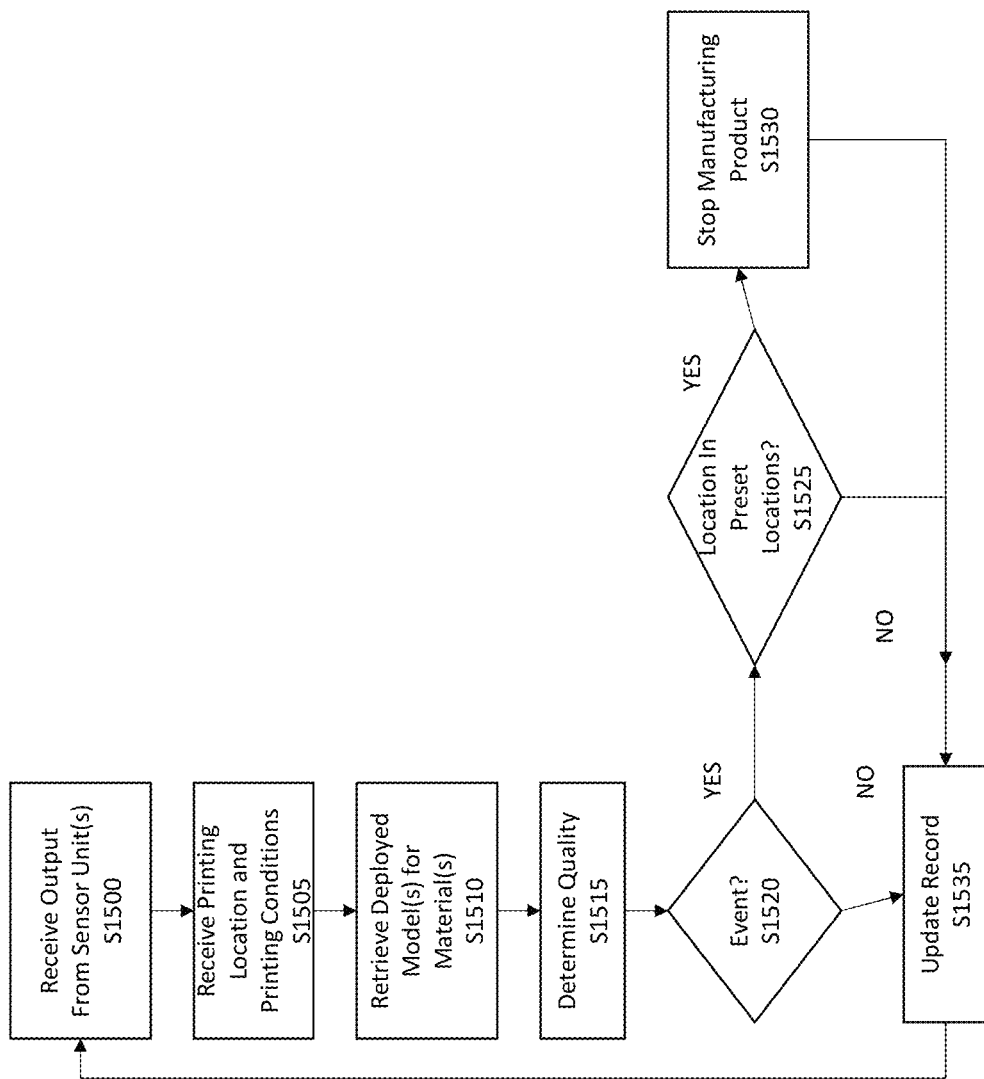
FIG. 15 is a flow chart illustrating a method in accordance with aspects of the disclosure.

FIG. 15 illustrates a method in accordance with aspects of the disclosure. This method may be used to determine whether there is an abnormality in the manufacturing process and whether to stop the manufacturing process due to the abnormality.

In accordance with aspects of the disclosure, the single board computer 20A may receive the output from each of the plurality of gas sensors in the sensor array 12 (gas sensors) at S1500. The output may be continuously received or periodically received. The period may be determined by a user via a GUI (similar to described above). The output from each gas sensor may be averaged. The number of readings that are averaged may be based on a user setting (also via the GUI).

The single board computer 20A may also receive the printing location and printing conditions from the controller 1320 at S1505. The printing location may be in x, y, z coordinates. The printing conditions were described above. S1500 and S1505 may occur at the same time. In an aspect of the disclosure, the printing conditions may be received prior to printing and the same condition is assumed for the entire process. In other aspects, the printing conditions are continuously updated and sent to the single board computer 20A on a pixel-by-pixel basis.

At S1510, the single board computer 20A may retrieved the deployed model(s) for the material(s) used in the additive manufacturing process (such as the polymer(s), metals or composite material(s). Where the same model is used for all materials, the single board computer 20A retrieves the one model. However, where different models are deployed based on the material(s), the single board computer 20A retrieves the model associated with the material(s) (identified in the printing conditions).

Based on the deployed model(s) and the received gas sensor output, the single board computer 20A may calculate the parameters used in the deployed model(s). For example, if the deployed model relies on one or more ratios of the gas sensor output, the single board computer 20A calculates the one or more ratios. Also, if the deployed model relies on a multiplication, addition, subtraction (weighted or unweighted), the single board computer 20A makes the appropriate calculation(s) needed for the model. After making the appropriate calculations, the processor 102 applies the model(s) to the calculated values to obtain the temperature and decomposition information based on the pattern of output from the gas sensors at S1515. For example, the pattern may predict a temperature and decomposition level based on the training/testing and correlations described above. Since the single board computer 20A receives the target temperature in the printing condition, if the model predicts a temperature that is different than the target temperature, the single board computer 20A may determine that an event has occurred at the pixel) (YES at S1520). While there may be a difference, the event may not indicate a decomposition in the material(s) (depending on the difference and the temperature). In an aspect of the disclosure, the single board computer 20A may examine the decomposition level predicted using the deployed model and the pattern of output from the gas sensors. If the decomposition level is greater than a threshold, the single board computer 20A may determine that there is an event at the pixel (YES at S1520). Otherwise, the single board computer 20A may determine that there is no event at the pixel (NO at S1520). When there is no difference in temperature (predicted and actual), the single board computer 20A may determine that no event has occurred at the pixel (NO at S1520).

When an event has been determined, the single board computer 20A may determine whether the event is at a key location (critical location) at S1525. This determination may be based on user defined information entered as part of the mechanical analysis described above. The pixel being manufactured is determined from the printing conditions received from the controller 1320. The pixel location is compared with key locations. When they coincide (YES at S1525), the single board computer 20A may transmit an instruction to the controller 1320 to stop the manufacturing process for the product at S1530.

The table 1400 for the pixel is updated with the determinations at S1535. For example, the table 1400 for the pixel is updated to include whether the printing is stopped or not, the predicted decomposition level and temperature (may be included in the chemical signature). In an aspect of the disclosure, the pattern of gas sensor outputs (outputs from the gas sensors may also be stored in the pixel record in the chemical signature (at S1500) and the printing conditions and other information) may be stored at S1505. When the manufacturing of the product is stopped, the product may be labelled as defective and recycled for reuse in other manufacturing processes.

The table 1400 may be used to generate a report. This report may be transmitted to the controller 1320 via a communication interface (wired or wireless).

Sensing Age/Quality of Food or Beverage

Figure 16:
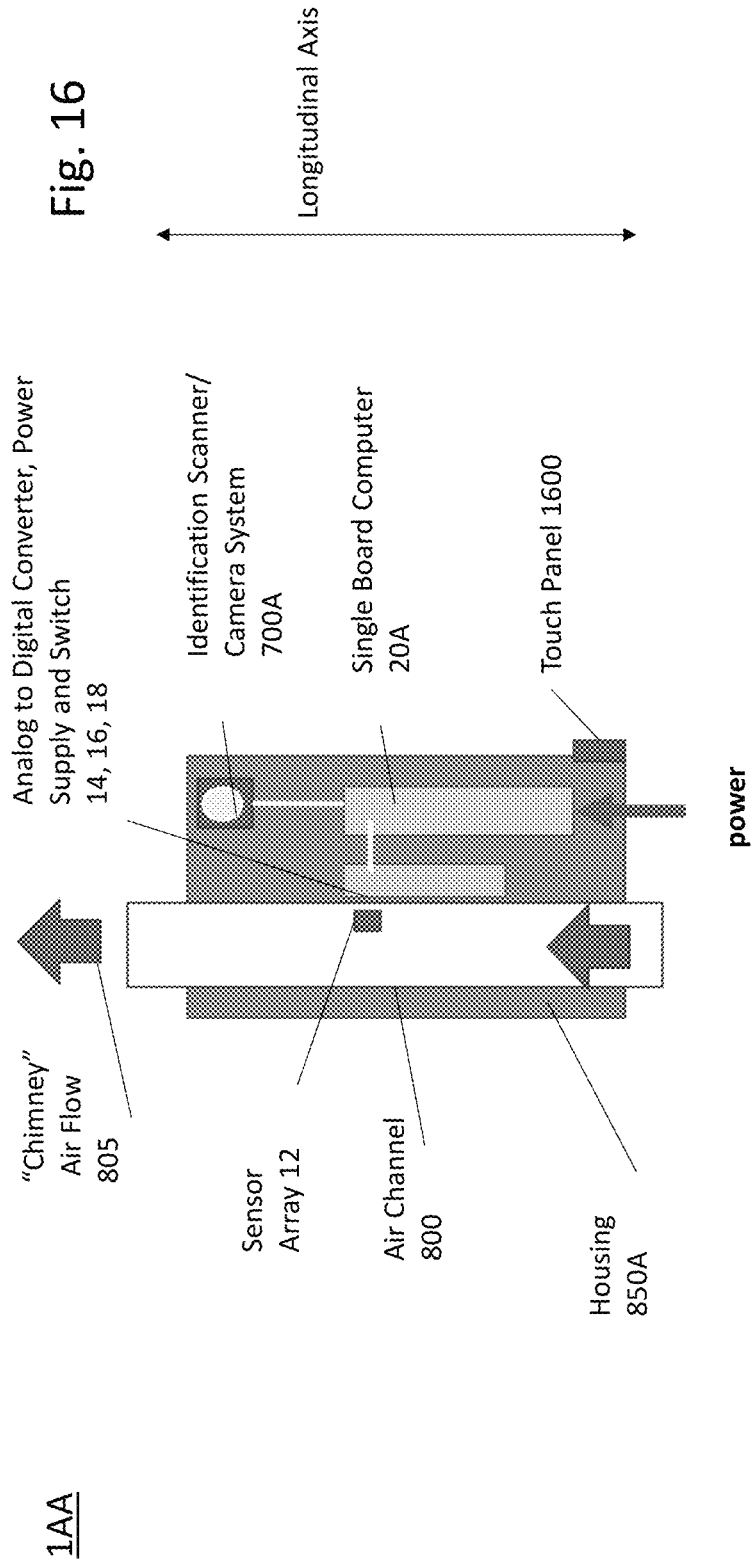
FIG. 16 is a diagram of another system in accordance with aspects of the disclosure.

In other aspects of the disclosure, a sensor system described herein similar to one described in FIG. 8 may be used to predict the age of a food or beverage and determine whether the quality of the food or beverage has deteriorated such as being spoiled. FIG. 16 illustrates an example of a sensor system 1AA in accordance with aspects of the disclosure. The sensor system 1AA may be a portable system such as handheld system. The system 1AA may have a handle (not shown). In other aspects of the disclosure, the sensor system 1AA may be mounted on the wall of a refrigerator. For example, the housing 850A may have a magnet such that the housing 850A may be attached to a magnetic surface of the refrigerator (door or wall). In other aspects, the sensor system 1AA may have a base or stand (not shown) such that the sensor system 1AA may be placed on a kitchen counter or on a shelf of the refrigerator. The stand or base may be hollow in order for the air to flow into the opening in the bottom of the housing 850 (and enter the air channel 800). The stand or base raises the bottom surface of the housing 850 to a distance above the counter or shelf.

In some aspects, the system 1AA may comprise fans for forcing air to flow through the air channel 800. However, given the configuration of the air channel 800 and gas sensors, the heat from the sensors causes movement via convection and therefore, fans may not be needed to have a constant flow.

The sensor system 1AA may have a display such as a touch panel 1600. The touch panel 1600 may receive an identification of a food or beverage for age and quality detection. In an aspect of the disclosure, the touch panel 1600 may have buttons in certain areas of the panel corresponding to foods or beverages. For example, one touch button may be for milk, another for food, such as beef and salmon. In other aspects of the disclosure, the touch panel 1600 may display a list of foods. For example, the list may include apples, bananas, pears, duck, etc . . . . In some aspects of the disclosure, the touch panel 1600 may display only food or beverage items that the sensor system 1AA have been trained and tested on. In another aspect of the disclosure, the touch panel 1600 may enable a user to manually enter the type of food or beverage by spelling out the name of the item.

In other aspects of the disclosure, instead of or in addition to the touch panel, the sensor system 1AA may comprise an identification scanner/camera system 700A. The identification scanner/camera system 700A may be configured to scan an identification code on the food or beverage such as on the package, such as a bar code scanner, a QR code scanner or a UPC code scanner. The identification code may convey to the sensor system 1AA the type of food or beverage and other manufacturing information including the recommended expiration date and packaged date.

In other aspects, the camera system 700A (image processor) may recognize the image of the food or beverage itself without a need for a package.

In an aspect of the disclosure, the sensor system 1AA may be trained and tested using a plurality of machine learning models to deploy a model for determining the age and quality of a food or beverage. Different models may be deployed for different types of foods. Additionally, different models may be deployed for different sub-types, brands or kinds within the type. For example, a different model may be deployed for red apples verse green apples. A different model may be deployed for different red apples. Different models may be deployed for different kinds of fishes or meats. For example, different models may be deployed for ground beef, rib-eye steaks or skirt steaks.

Model(s) may be deployed in a similar manner as described above in FIG. 10. In order to train/test the plurality of models (and subsequently determine which to deploy for a particular type or sub-type), a dataset for training and testing is obtained.

In an aspect of the disclosure, each item of food or beverage may be separately trained/tested.

An untrained/untested food or beverage item may be trained/tested by either scanning the item (package) as described above, the type entered via the touch panel 1600 or the type recognized by image processing of an image of the food or beverage acquired by the camera system 700A. In an aspect of the disclosure, the sensor system 1AA may have a wired or wireless communication interface and search the Internet to recognize the image of the food or beverage (via the single board computer 20A) acquired by the camera system 700A. Since this is the first time the food or beverage is scanned, imaged or entered into the sensor system 1AA, the sensor system 1AA will recognize that a model has not been created for the item and may enter a training/testing mode. The single board computer 20A may initiate a record in the memory for the food or beverage item. The record may include a food index and food name. When the identification code of the food or beverage is read, the amount of the item, recommended expiration date, packaging date and other information may also be recorded in the record. When there is no packet, the single board computer 20A may obtain information such as recommended expiration date, recommended storage temperature from the Internet, such as, from the Food and Drug Administration (FDA). In an aspect of the disclosure, even if the packet has an expiration date, the single board computer 20A may obtain a recommended storage lifetime (expiration date) from the Internet, such as from the FDA.

The food or beverage item is subsequently exposed to the sensor array 12 and the output of the gas sensors is obtained by the single board computer 20A, averaged (if needed) and recorded with the time, e.g., day. This pattern of gas sensor output is taken as a baseline for the food (e.g., day 1). The system 1AA assumes that the first time the item is sensed is a fresh food or beverage. In an aspect of the disclosure, the time of the day may also be recorded in addition to the date. The food or beverage item may be kept near the opening on the bottom of the housing 850A for one or more minutes such that the gas sensors in the sensor array 12 reach equilibrium. The start of averaging of the sensor output may commence after the equilibrium period. The temperature and pressure in the area may also be recorded. This is because the gas sensor output may be different in different temperatures/pressures such as on a counter verse in a refrigerator. In accordance with this aspect of the disclosure, the sensor system 1AA may have a temperature sensor which is used for calibration of the sensor array 12.

Additional data points may be subsequently acquired at different dates/times. The frequency of acquiring the data points may depend on the type of food or beverage, and how quickly the item deteriorates and spoils. For example, for a food or beverage item with a long shelf (storage lifetime) or an expiration date in the far into the future, fewer frequent data points may be needed than for a food or beverage item with a short shelf (storage lifetime) such as fruits, meats or fish. For longer shelf (storage lifetime) items, data points may be obtained once a week. However, for shorter shelf (storage lifetimes) or items expiring quickly, data points may be obtained daily or even twice a day. In some aspects, the frequency may not be the same over the life of the item (food or beverage). For example, initially, data points may be obtained once a week, however, as the item nears is expiration date or storage lifetime, data points may be acquired more frequently (such as daily or twice a day). Additionally, even though an item has past its "expiration date" or "storage lifetime" it does not mean the food or beverage is "spoiled" or deteriorated. Therefore, in some aspects, data points may be acquired even after the expiration date or storage lifetime. The frequency of acquiring the data points after the expiration date or recommend storage lifetime may be even more frequency since there is a higher likelihood that the food or beverage item has spoiled or deteriorated.

At each data points, since different single food or beverage items may be trained/tested simultaneously, the food or beverage item may be scanned/imaged/input such that the single board computer 20A recognizes the item and adds the sensed pattern (and date) to the correct record. When all desired data points for a specific food or beverage item are acquired, the user may press a button or indicate finished.

Once all the data points are acquired for a particle food or beverage item (and correlated with a date), the single board computer 20A divides the dataset collected into datasets for training and testing as described above.

Also as described above, a plurality of machine learning (ML) models may be trained using different combinations of hyperparameters using the training set. The plurality of ML models includes models from different ML techniques including random forest, neural networks and support vector regression algorithms. The sets of hyperparameters may be randomly selected. For example, the hyperparameters for random forest include number of trees in the forest and depth of each tree. The hyperparameters for a neural network include number of hidden layers, number of nodes within each hidden layer, and an optimizer, The hyperparameters for the support vector regression algorithm include Kernel, C, and epsilon.

The number of plurality of ML models trained (and tested) may be application specific or a user parameter. For example, 10000 different models/hyperparameter sets may be trained where FIG. 10 shows an example of the bounds of the hyperparameters that may be used.

Different combinations of the sensor outputs (patterns) may be evaluated in the training. For example, ratios of the sensor outputs may be used in the training. In addition, the individual outputs of the gas sensors in the sensor array 12 may also be inputs to the models.

In some aspects, only the sensor outputs that have a high sensitivity may be used in the training. In some aspects of the disclosure, models may be trained to reach a predetermined percentage accuracy. For example, the predetermined percentage may be 95%. If a model does not exceed the predetermined percentage, additional data may be acquired for different days and or amounts.

The trained models may be tested using the testing set (data from each cross-validation split). In an aspect of the disclosure, the performance of each model may be determined using a parameter such as root mean square error (RMSE). RMSE may be determined based on the actual age of the food or beverage item verses the predicted age of the food or beverage item using the model.

The highest performing model from among the plurality of ML models trained and tested may be selected for deployment. For example, the single board computer 20A compares the RMSE from each model and selects the model with the smallest RMSE. This model is subsequently used for sensing. The selected model is stored in memory.

During the training/testing, a specific pattern may be assigned or identified as corresponding to the expiration date. Additionally, thresholds such as specific sensor patterns or a specific age may be added to the model or correlated to the model such that if the sensor pattern output by the gas sensors in the sensor array 12 are predicted to be the specific age or later, the food or beverage item may be deemed to be spoiled. The specific age may be determined based on tasting of the item. Additionally, the specific age may also be based on user visual inspection. In other aspects, the specific age may be based on information from the FDA. In an aspect of the disclosure, a percent spoilage may be determined based on the specific age or specific sensor pattern. For example, a new item may have a zero (0%) spoilage and an expired item may have 100% spoilage. The percent spoilage may be linear interpolated based on the specific sensor patterns detected. In other aspects, a non-linear interpolation may be used. In other aspects, a combination of non-linear interpolation and linear interpolation may be used where an average of the non-linear and linear interpolation may be used for the predicted spoilage percentage.

The above process may be repeated for each food or beverage item desired for age detection.

In some aspects, a model may be deployed for a combination of food items or beverage items in a similar manner as described above. For example, a salad may contain multiple items such as lettuce, carrots, tomatoes, cucumbers, dressing, etc. The model for the combination of items may be trained/tested and deployed in a similar manner as described above (where the dataset is acquired over time starting with a baseline).

Figure 17:
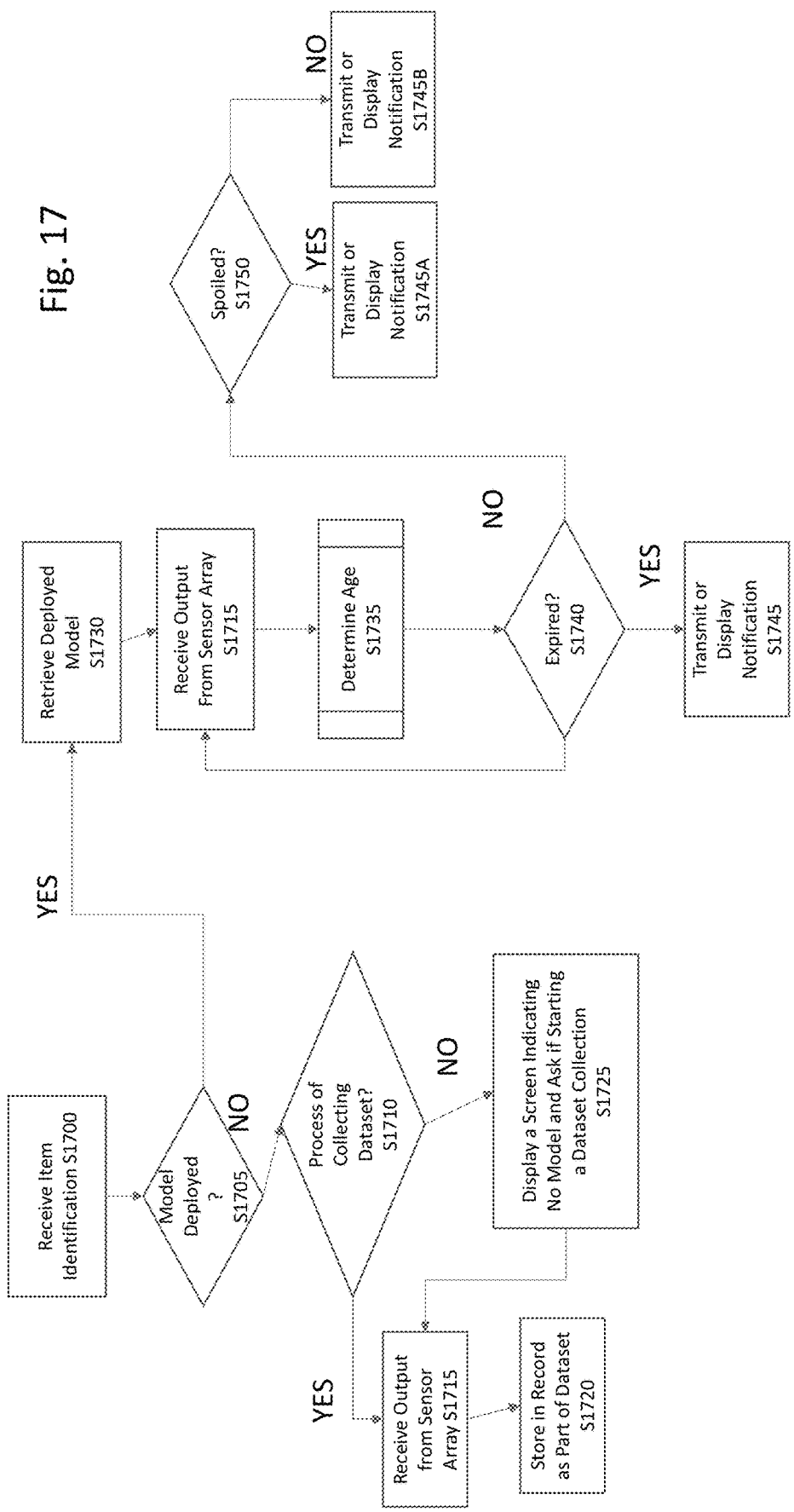
FIG. 17 is a flow chart illustrating a method in accordance with aspects of the disclosure.

FIG. 17 illustrates a method in accordance with aspects of the disclosure. This method may be used to predict whether an item of food has expired, is spoiled (even though the date is prior to the recommend expiration date) and percentage of spoilage (and to enter a training/testing mode).

At S1700, the sensor system 1AA receives an identification of a food or beverage item. The identification may be received via the identification scanner (UPC code, bar code, QR code) or image recognition from an image acquired via the camera system 700A or via the touch panel 1600, as described above. In response to the receipt of the identification, the single board computer 20A may determine whether a model has been deployed for the item. The single board computer 20A checks the memory for the stored model associated with the food or beverage item, e.g., for the type by name. When the single board computer 20A determines that a model for the food or beverage item has not been deployed (NO at S1705), the single board computer 20A may determine if the dataset collection process has already started, e.g., in the middle and not completed at S1710. The single board computer 20A checks if a record for the food items has been opened in the memory and whether a data point having an associated time and sensor pattern has been stored. When the single board computer 20A determines that a record is opened and a data point is stored (but not competed) (YES at S1710), the single board computer 20A subsequently receives the output from the sensor array (and averages) at S1715 and stores the pattern as a data point in the dataset at S1720. The single board computer 20A may display a screen asking if the dataset for the item is compete. When the dataset for the item is complete, the single board computer 20A divides the dataset is described above for training/testing.

When the single board computer 20A determines that a record is not opened and it is the first time the item is scanned (or identified to the system 1AA), the single board computer 20A may display a screen on the touch panel 1600 indicating that no machine learned model is deployed for the item and request whether the user would like to start creating the dataset for deploying a model at S1725.

When the single board computer 20A determines that a machine learned model has been deployed for the food or beverage item (or combination of foods or beverages), the single board computer 20A retrieves the machine learned model from the memory for the item and awaits the output from the sensor array 12. At S1715, the receives the output from the sensor array (and averages).

At S1735, the single board computer 20A predicts the age of the food or beverage item based on the output pattern from the sensor array 12 and the deployed machine learning model. For example, based on the deployed model(s) and the received gas sensor output, the single board computer 20A may calculate the parameters used in the deployed model(s). For example, if the deployed model relies on one or more ratios of the gas sensor output, the single board computer 20A calculates the one or more ratios. Also, if the deployed model relies on a multiplication, addition, subtraction (weighted or unweighted), the single board computer 20A makes the appropriate calculation(s) needed for the model. After making the appropriate calculations, the single board computer 20A applies the model(s) to the calculated values to obtain a predicted age and quality based on the one or more combinations of output from the gas sensors At S1740, the single board computer 20A determines, when the predicted age coincides with the pattern associated with an expiration date (even if the expiration date is not yet reached), that the item is expired. The single board computer 20A may also determine whether the current date is after the recommended expiration date stored in the record for the item (from the FDA or from the package). If either determination is YES at S1740, the single board computer 20A may display a notification in the form of a warning on the touch panel 1600 at S1745. In some aspects, the single board computer 20A may transmit a notification to a predetermined device, such as a mobile phone indicating that the product has expired. In some aspects, the indication may distinguish whether the current date is after the recommended expiration date (expiration date) or whether the aroma from the item indicates that the product has an aroma similar to the aroma at the expiration date (predicted date).

At S1750, the single board computer 20A may determine whether the food or beverage item is spoiled. In an aspect of the disclosure, different combinations of sensor outputs (or a predicted age) may be correlated to a spoiled condition or a percentage of spoiled condition when the model is deployed (the correlated may be entered into the dataset).

At S1750, the single board computer 20A may determine whether the sensor output acquired in response to the food or beverage item or predicted age using the sensor output as the input to the deployed model is sensor pattern or predicted age correlated to a spoiled condition (or percentage) or is a predicted age older than an age that is correlated to the spoiled condition (or percentage). When either of these determinations is YES, the single board computer 20A may determine that the item is spoiled at S1750 (YES) and may display a different notification on the touch panel 1600 at S1745A. The different notification may be in a different color. In other aspects, the notification may have words in CAP or BOLD or a danger symbol. When the item is not spoiled (NO at S1750), the single board computer 20A may display a different notification on the touch panel 1600 at S1745B. The different notification may be in a different color. For example, when the item is neither expired or spoiled, the display may be green, when the item is expired, the display may be yellow and when the item is spoiled, the display may be red. Similar to above, the notifications may be transmitted to another device such as a mobile device. Contact information for the other device such as the mobile device may be registered in the memory of the single board computer 20A.

In other aspects of the disclosure, instead of or in addition to, the sensor system 1AA may determine the age and quality of food or beverage item based on analysis of images of the item. Similar to training/testing/deployment using patterns of the sensed output from gas sensors in an array 12, the training/testing/deployment may also be done using images of the item taken at different times. As foods and beverages age, the color of the items may change. This discoloration may be analyzed, and a model may be deployed based on the analysis.

In some aspects of the disclosure, the images used for training and testing for an item may be obtained from the Internet. The single board computer 20A based on an instruction to deploy a model for an item may obtain multiple images from the Internet and descriptors of the images. The images may include a baseline (new food or beverage), expired food or beverage and spoiled food or beverage. The images may be correlated to the descriptors. In other aspects of the disclosure, the images used for training and testing may be acquired when the sensor patterns of obtained from the gas sensors in the array 12. For example, when that item is held near the opening, the items may also be held in the line of sight of the camera system 700A. In an aspect of the disclosure, the deployed model may be generated using both the images of the item and the outputs from the sensor array 12. As such, the determinations of age, expired and spoiled may be based on both acquired current images of the item and the sensor outputs from the sensor array 12.

Natural Language Descriptor

In other aspects of the disclosure, a sensor system described herein similar to one described in FIG. 8 may be used to predict a natural language descriptor(s) associated with an item. The items may be food such as fruits, vegetables, meats, fish, nuts, spices, herbs, dairy products and cereal. The items may be beverages such as alcoholic beverages scotch, brandy, wine, whisky, beer, non-alcoholic beverages such as coffee, tea, sodas, juices, etc. The items may also be seeds, flowers, trees, etc.

A known current system approach is to assign natural language descriptors characterizing aroma to a particular chemical associated with the aroma. In the known system, the data may be processed using principal component analysis, multivariable curve regression techniques to define correlation between sensor signals and associated aroma. If a tested aroma is within the boundaries of classified standard aromas it can be identified as belonging to one or another class. One problem with the current approach is the complexity of aromas comprising a mixture of several components, which lead often times to incorrect identification of the aromas.

In an aspect of the disclosure, the system 1A acquires the sensor output and processing the same to predict complex aroma patterns without using the chemical structure, PCA or MCR analytics using a centroid approach. The aromas may be converted to the natural language descriptors using individual sensor output and/or ratios of the sensor outputs. In an aspect of the disclosure, a logistic regression model may be used to predict the natural language descriptors for the aroma and a confidence (percent confidence).

In an aspect of the disclosure, the logistic regression model may be trained and tested to predict the natural language descriptor(s) of the item sensed. In this aspect of the disclosure, the sensor system 1A may a user interface such as a touch screen such that a user may enter a training mode and input the natural language descriptor(s) and a coefficient for each during the acquisition of a dataset for training and testing. In an aspect of the disclosure, the camera system 700 may be omitted. A matrix of samples may be created. The columns in the matrix may be the natural language descriptors and the rows may be the samples. If aroma descriptor is not present in the sample, the coefficient in the matrix is zero. If aroma is present in the same, the coefficient of the cell in the matrix is larger than zero. If several aroma descriptors are present, the coefficients of corresponding columns are more than zero. The dominant descriptor is characterized by larger coefficient among other coefficients characterizing the sample. The weakest aroma descriptor has the smallest non-zero coefficient among other descriptors for the same sample. A sum of all aroma descriptors for a sample is equal to one, and individual descriptors correspond to the fractional intensity of a particular aroma descriptor (zero or >zero). The size of the matrix is the number of samples x the number of aroma descriptors. If the item has a known natural language descriptor such as from a manufacturer or a flavor wheel, the user may enter the natural language descriptors and coefficients based on the available information. However, if the item does not have a known natural language descriptor(s), an expert may smell the item and provide the natural language descriptor for the item and coefficient(s).

Each item for the dataset may be brought near the housing 850 and held below the air channel to allow thermal convection from high temperature of sensors to draft air with aroma into. In other aspects, a fan may be used to move the air into the air channel. For each sensor in the array the rise time of the signal as well as a value of stabilized signal response are measured for all samples. Therefore, each reference sample may have an array of sensor responses and an array of sensor response rise time.

The name of the item may also be entered. The name may be used to confirm that this is a new item for training/testing as opposed to the same item being included having a different age.

In an aspect of the disclosure, another matrix may be generated. The size of this matrix may be number of samples x. number of sensors. In an aspect of the disclosure, additional matrixes may be generated with ratio of sensor responses (and rise time). Each matrix may have a different sensor response ratio, e.g., S1/S2 and S2/S3.

The samples may be divided for training and testing and the model trained and tested using the respective dataset. Cross-validation may be used such that all of the samples may be used for training. In an aspect of the disclosure, the training is done until a preset accuracy threshold is reached. For example, the predetermined percentage may be 95%. If a model does not exceed the predetermined percentage, additional data may be acquired for different samples. Further, in some aspects, only the sensor outputs that have a high sensitivity may be used in the training.

At least two items are used for training and testing. However, the larger number of items used for training and testing, the better the prediction is of the natural language descriptor. There is a plurality of natural language descriptors. For example, there may be 10 descriptors of the aroma. In an aspect of the disclosure, there may be different descriptors based on the type of the item. For example, the natural language descriptors for coffees may be different from wines, or teas, which also may be different for hops.

In an aspect of the disclosure, when a precent remaining or precent degradation (also referred to a precent depletion) is determined additional measurements are done for samples which are allowed to degrade their aroma (for instance samples are kept in the open air for day, two . . . week). For each day the sensor response is measured for all reference samples. In an aspect of the disclosure, the user may input the identifier or type of the sample and the day, e.g., day 2, day 5, day 10 . . . etc. . . .

When all desired data points for a specific item are acquired, the user may press a button or indicate finished.

As described above, both individual and different combinations of the sensor outputs (patterns) may be used in the model. For example, ratios of the sensor outputs may be used in the training. In some aspects of the disclosure, two different gas sensor ratios may be obtained. In some aspects, three or more gas sensor ratios may be obtained.

Figure 18:
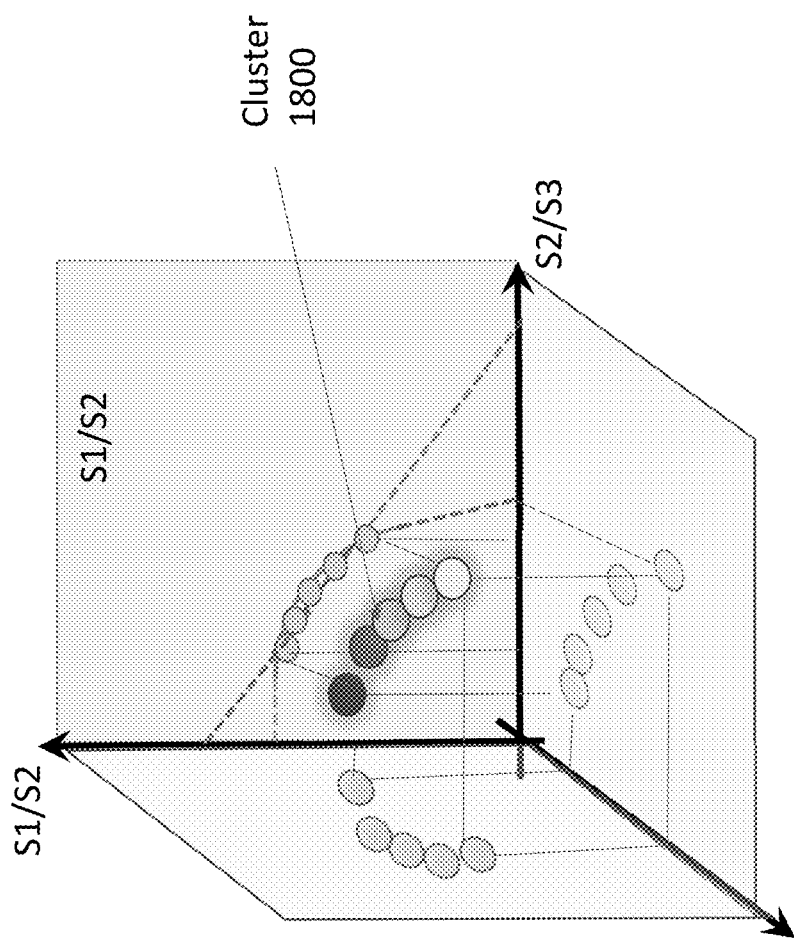
FIG. 18 is an example of a cluster of sensor output ratios in accordance with aspects of the disclosure.

Aromas associated with the same natural language descriptors may be clustered in three-dimensional space (centroids). FIG. 18 shows an example of a cluster 1800 in three-dimensional space of a gas sensor pattern taken using three ratios of outputs, S1/S2, S1/S3 and S2/S3. The outputs may be projected into 2-D planes. Three projections are also shown in FIG. 18. The different clusters, e.g., different patterns, may be used train the model to predict the natural language descriptors.

Figure 19C:
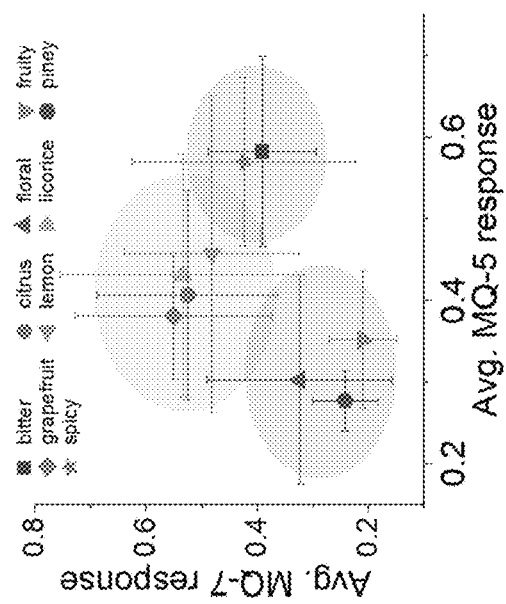
Figure 19B:
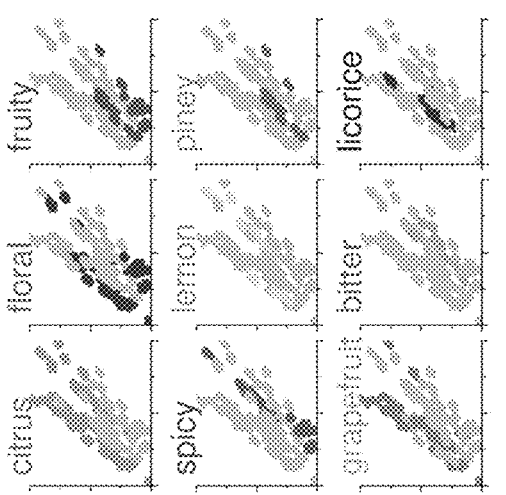
Figure 19A:
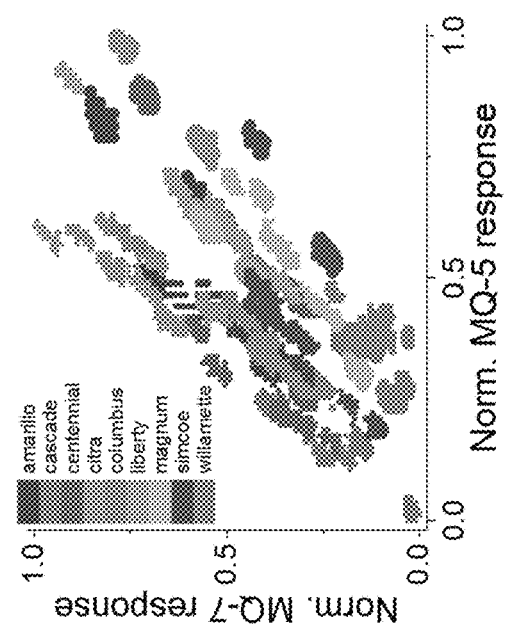

FIGS. 19A-19I illustrates an example of a dataset acquired from 9 different hops over 18 days. FIG. 19A is an example of a scatter plot of normalized MQ-7 and MQ-5 sensor responses over 18 days of exposure to hops aromas. The size of points in the plot represents days (the smallest points were measured on day 1 and the largest points were measured on day 18). FIG. 19A shows data from day 1, 2, 3, 4, and 18. FIG. 19A shows the nine different hops with clustered responses for the normalized sensor responses. FIG. 19B shows the same scatter plot, however, it is identified using the natural language descriptors. FIG. 19C shows centroids of each natural language descriptor. In FIG. 19C there is an error bar showing a standard deviation. Aromas may be naturally clustered into three groups: piney/floral/fruity, grapefruit/citrus/licorice/lemon, and spicy/bitter, schematically represented by transparent ellipsoids. As can be seen in FIGS. 19B and 19C, in many cases, the aromas having the same natural language descriptor are clustered in the same specific regions. The centroid of each aroma provides a map for direct correlation of sensor response to the natural language descriptors. Once the centroid coordinates are known, the model can be constructed which maps a vector of MQ-X gas sensor responses to the most probable aromas associated with those responses as described herein.

Figure 19I:
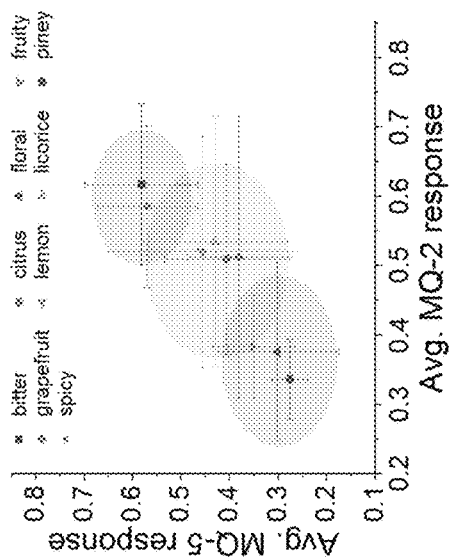
Figure 19H:
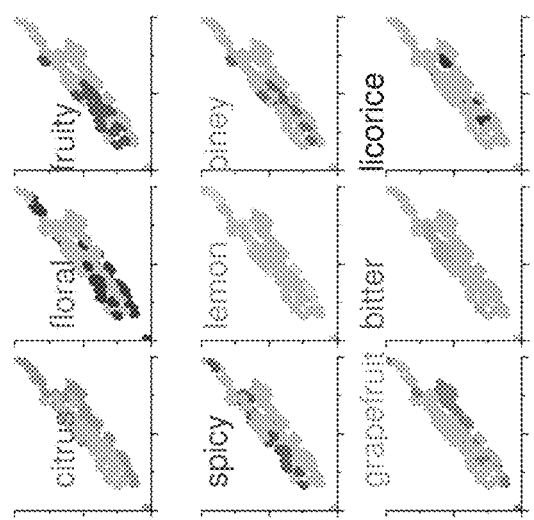
Figure 19G:
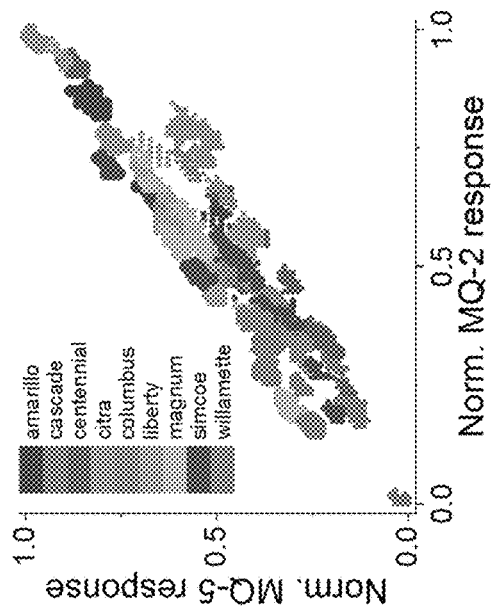

FIG. 19D-19F illustrate similar graphs as described above for the normalized MQ-7 and MQ-2 sensor responses over 18 days of exposure to hops aromas. FIG. 19G-19I illustrate similar graphs as described above for the normalized MQ-5 and MQ-2 sensor responses over 18 days of exposure to hops aromas. As can be seen in FIGS. 19B, 19C, 19E, 19F, 19H and 19I, in many cases, the aromas having the same natural language descriptor are clustered in the same specific regions. The centroid of each aroma provides a map for direct correlation of sensor response to the natural language descriptors. Once the centroid coordinates are known, the model can be constructed which maps a vector of MQ-X gas sensor responses to the most probable aromas associated with those responses as described herein. This also suggests that different combinations, such as ratios of the sensor outputs and/or ratios in combinations with absolute individual sensor responses, may be used to increase the clustering and differentiation.

In an aspect of the disclosure, when the model is trained and meets the performance requirement(s), the user may press a button to indicate that the system (e.g., 1A) is ready for prediction (e.g., prediction).

Figure 20:
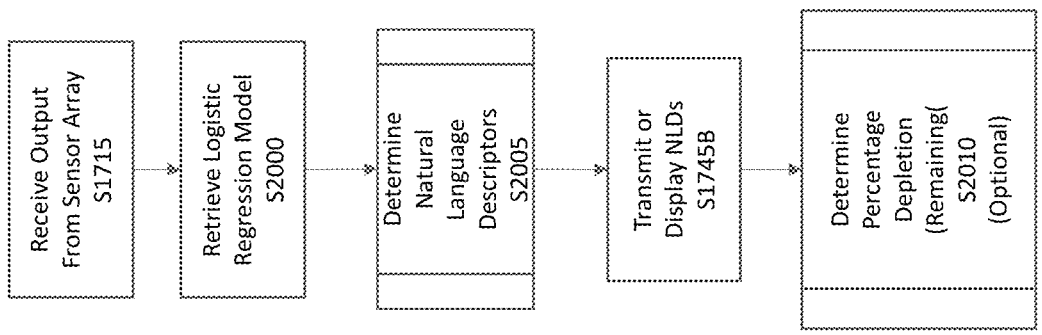
FIG. 20 is a flow chart illustrating a method in accordance with aspects of the disclosure.

FIG. 20 illustrates a method in accordance with aspects of the disclosure. This method may be used to predict the natural language descriptors associated with an aroma and a confidence. At S1715, an item may be brought near the housing 850 and held below the air channel to allow thermal convection from high temperature of sensors to draft air with aroma into. In other aspects, a fan may be used to move the air into the air channel. For each sensor in the array the rise time of the signal as well as a value of stabilized signal response are measured. The single board computer 20A receives the output from the sensor array 12. The single board computer 20A retrieves the trained and tested logistic regression model at S2000. At S2005, the single board computer 20A uses the model to predict the natural language descriptors associated with an aroma and a confidence. When the model uses ratios of the sensor output, the single board computer 20A calculates the ratio(s). The model outputs the probabilities for natural language descriptors. For example, the model may be trained to recognize three identifiers: [sweet, sour, bitter]. In this case, the model may then output an array such as OUTPUT=[0.25, 0.7, 0.05]. In this case, the model is predicting that there is 25% chance of sweet aroma, 70% of sour aroma, and 5% of bitter aroma. This information tells us the percent confidence in each detected aroma, and which aroma was the primary aroma (the aroma with the highest percentage), and which other secondary aromas were detected. When there are multiple natural language descriptors used in the training, any natural language descriptor that is not predicted may have a value of 0, which means that the aroma is not detected with any degree of confidence. For example, the output may be OUTPUT=[[0.25, 0.00, 0.00, 0.7, 0.00, 0.00, 0.05]. In this example, four natural language descriptors of the seven natural language descriptors are not predicted with any degree of confidence. In some cases, the model might predict an OUTPUT=[0.96, 0.01, 0.03]. In this case, there is one dominant/primary aroma (with 96% probability), e.g., sweet, and that the other aromas, e.g., sour and bitter aromas were not detected with any degree of confidence (only 2% and 3% respectively).

At S1745B, the single board computer 20A may output the results of the prediction. In some aspects of the disclosure, the single board computer 20A may cause the results to be displayed on a display. The percentages may be displaying in order of confidence. For example, the natural language descriptor with the highest confidence may be displayed first. Using the above example where the OUTPUT=[0.25, 0.7, 0.05], the display may display, 70% sour aroma, 25% sweet aroma and 5% bitter aroma. In other aspects, the display may only display the primary natural language descriptor. In other aspects, there may be a confidence threshold, and the display may only display natural language descriptors having a confidence above the confidence threshold. A user may set the confidence threshold. In other aspects, the display may display all of the natural language descriptors having a confidence above zero (or all descriptors with the respective confidence including zero). Instead of and/or in addition to displaying the natural language descriptors and confidence, the single board computer 20A may transmit the same to a device via text or an email.

At S2010, the single board computer 20A may determine the percent remaining or depletion of the aroma(s). In an aspect of the disclosure, the user may input into the system 1A the type of the item that is the target of the determination. Similar to above, the user may use the touch panel display to input the type. As noted above, in a training/testing mode, measurements may be done for samples which are allowed to degrade their aroma (for instance samples are kept in the open air for day, two . . . week). Based on the input type, the single board computer 20A may retrieve the dataset for the type. The output of one or more sensors or ratios of the output of one or more sensors having the largest changes over the measurement may be selected to evaluate the degradation of the aroma (depletion or remaining percent). The change may be plotted in x and y coordinates for visualization and/or interpolation.

Figure 21:
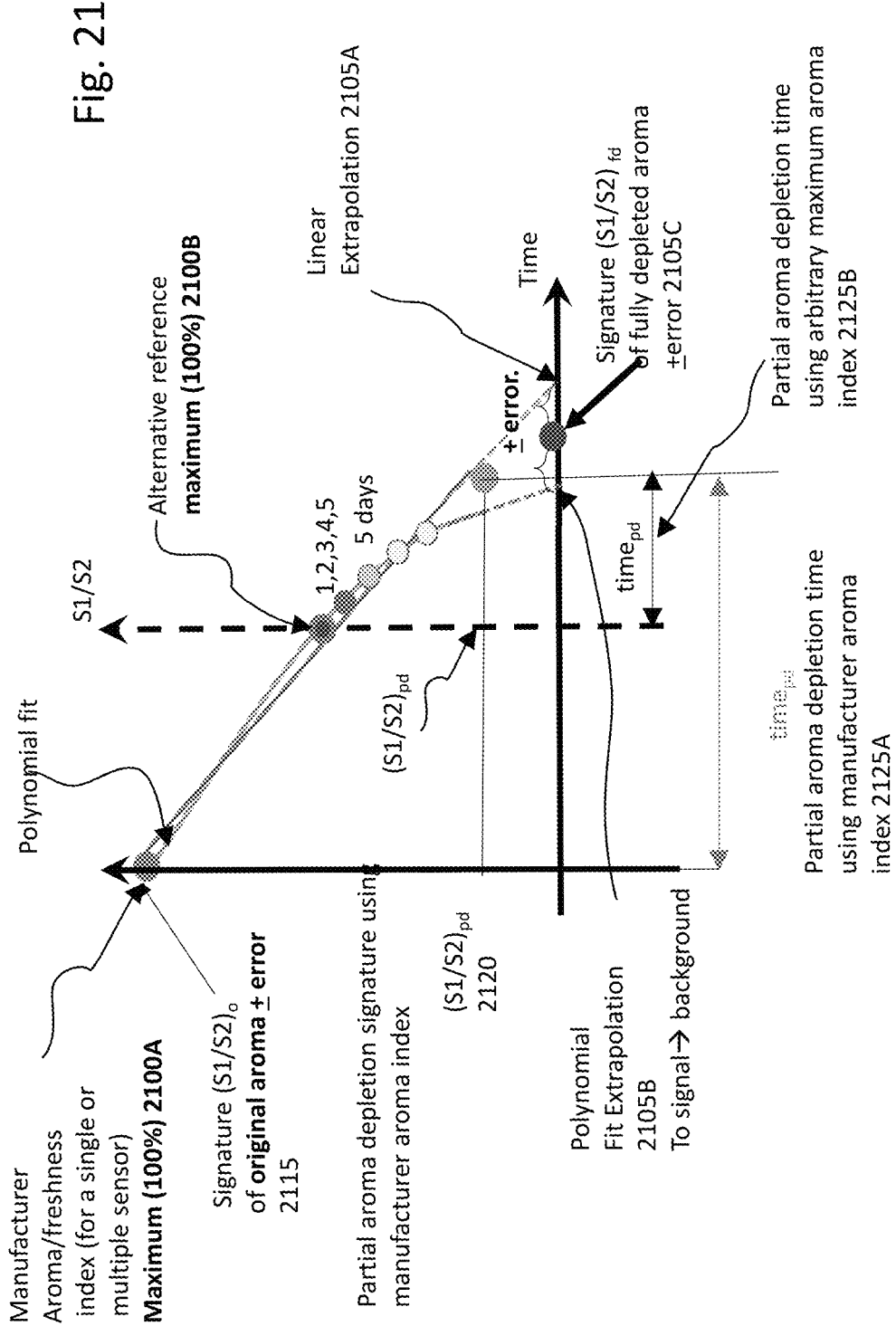
FIG. 21 is an example of sensor output at different times for a sample and determination of partial aroma depletion in accordance with aspects of the disclosure.

FIG. 21 illustrates an example sensor ratio changing over 5 days of measurements. The sensors are identified as S1 and S2 (ratio S1/S2). However, as noted above, individual sensor output may also be used. The time is on the x-axis and ratio value is on the y-axis. A reference, e.g., 100% maximum aroma may be determined. In an aspect of the disclosure, the manufacturer of the item may provide an aroma/freshness index 2100A. A dot on the y-axis at T=0 shown in FIG. 21 represents the value.

The index may include information of a single sensor, multiple sensors and/or one or more ratios. This is the measurement when the item is manufactured (new). In other aspects of the disclosure, when the item is first opened and its initial measurements are obtained by the system (e.g., 1A), these measurements may be used as the maximum reference 2100B. A dot which intersects a vertical dashed line represents this value. (day 1 measurement). Dots (circles) are also shown representing the ratio of sensor outputs in day 2-5 (ratio decreases). As can be seen in FIG. 21, the change is non-linear. To approximate full degradation (depletion and zero remaining), both linear and polynomial fit may be used. The linear extrapolation 2105A is shown at the end of a dashed straight line and the polynomial fit extrapolation 2105B is shown to the left of the linear extrapolation 2105A. The signature for S1/S2 representing fully depletion aroma 2105C may be obtained from averaging 2105A and 2105B (+− error). Full depletion aroma 2105C is shown on the x-axis with a dot (the outputs of the sensors effectively would equal the background).

Also, once the linear extrapolation 2105A and the Polynomial fit extrapolation 52105B is determined, when the alternative reference 2100B is used, linear extrapolation and polynomial fit may be used to determine the ratio at T=0. The signature 2115 at T=0 may be an average of the two (+− error).

FIG. 21 also shows an arbitrary ratio representing a ratio of measured sensor output at an unknown time, e.g., $S1/S2_{pd}$ 2120. Once the 2105C and 2115 are determined, the time on the x-axis associated with the ratio of the sensor output may be determined using interpolation.

The time (pd) (partial depletion or remaining amount) is shown from both the manufacture aroma index 2100A and the alternative reference 2100B (e.g., 2115A and 2125B). This may be the predicted age of the item.

The remaining amount of the aroma(s) from a single sensor or ratio may be determined from the current sensor output or ratio divided by the difference between the sensor output or ratio at both T=0 (either 2100A or 2115) and T=full depletion (2105C) times 100%. The partial depletion is the complement (1-remaining amount). For example if the ratio $(S1/S2)_{pd}$ is 20% than there is a 80% partial depletion.

The above process may be repeated for each selected sensor output and ratio, e.g., determining 2100A or 2100B, 2105A, 2105B, 2105C (and corresponding total depletion time), 2115 (if 2100A is not available), and $time_{pd}$ 2125A and 2125B

Similar to above, a remaining amount of the aroma(s) may be calculated from an average of each individual determination (replace the 2100A or 2115 and 2105C with the average and use the average sensor outputs or ratios of the outputs). When the standard deviation is larger than first percentage, it may be an indication that there is a larger discrepancy in sensor reading and need to down select a lesser number of sensor outputs and/or ratios to average. The down selection may continue until the standard deviation is less than a second percentage. In an aspect of the disclosure, the first percentage may be 15% and the second may be 10%.

As used herein terms such as "a", "an" and "the" are not intended to refer to only a singular entity, but include the general class of which a specific example may be used for illustration.

As used herein, terms defined in the singular are intended to include those terms defined in the plural and vice versa.

References in the specification to "one aspect", "certain aspects", "some aspects" or "an aspect", indicate that the aspect(s) described may include a particular feature or characteristic, but every aspect may not necessarily include the particular feature, structure, or characteristic. Moreover, such phrases are not necessarily referring to the same aspect.

Various aspects of the present disclosure may be embodied as a program, software, or computer instructions embodied or stored in a computer or machine usable or readable medium, or a group of media which causes the computer or machine to perform the steps of the method when executed on the computer, processor, and/or machine. A program storage device readable by a machine, e.g., a computer readable medium, tangibly embodying a program of instructions executable by the machine to perform various functionalities and methods described in the present disclosure is also provided, e.g., a computer program product.

The computer readable medium could be a computer readable storage device or a computer readable signal medium. A computer readable storage device may be, for example, a magnetic, optical, electronic, electromagnetic, infrared, or semiconductor system, apparatus, or device, or any suitable combination of the foregoing; however, the computer readable storage device is not limited to these examples except a computer readable storage device excludes computer readable signal medium. Additional examples of the computer readable storage device can include: a portable computer diskette, a hard disk, a magnetic storage device, a portable compact disc read-only memory (CD-ROM), a random access memory (RAM), a read-only memory (ROM), an erasable programmable read-only memory (EPROM or Flash memory), an optical storage device, or any appropriate combination of the foregoing; however, the computer readable storage device is also not limited to these examples. Any tangible medium that can contain, or store, a program for use by or in connection with an instruction execution system, apparatus, or device could be a computer readable storage device.

A computer readable signal medium may include a propagated data signal with computer readable program code embodied therein, such as, but not limited to, in baseband or as part of a carrier wave. A propagated signal may take any of a plurality of forms, including, but not limited to, electromagnetic, optical, or any suitable combination thereof. A computer readable signal medium may be any computer readable medium (exclusive of computer readable storage device) that can communicate, propagate, or transport a program for use by or in connection with a system, apparatus, or device. Program code embodied on a computer readable signal medium may be transmitted using any appropriate medium, including but not limited to wireless, wired, optical fiber cable, RF, etc., or any suitable combination of the foregoing.

The terminology used herein is for the purpose of describing particular aspects only and is not intended to be limiting the scope of the disclosure and is not intended to be exhaustive. Many modifications and variations will be apparent to those of ordinary skill in the art without departing from the scope and spirit of the disclosure.

What is claimed is:

1. An additive manufacturing system comprising:
a first electronic nose and a second electronic nose, the first electronic nose being mounted to a first side of an extruder head and the second electronic nose being mounted to a second side of the extruder head, each said electronic nose comprising:
a housing having openings on corresponding ends thereof to enable air flow, the housing having an air channel for air to flow between the ends;
a plurality of thin film gas sensors, each having an active sensor portion in the air channel; and
a mount configured to mount the housing to the extruder head of an additive manufacturing device, and
a processor configured to:
supply power to the plurality of thin film gas sensors to bias the sensors;
receive output from each of the plurality of thin film gas sensors;
determine whether there is an abnormality in an additive manufacturing process manufacturing a product from one or more materials or composite materials based on one or more combinations of the output from each of the plurality of thin film gas sensors during the additive manufacturing process and from a deployed machine learning model; and
generate a report for the additive manufacturing process containing the abnormality determination.

2. An additive manufacturing system comprising:
at least one electronic nose comprising:
a housing having openings on corresponding ends thereof to enable air flow, the housing having an air channel for air to flow between the ends;
a plurality of thin film gas sensors, each having an active sensor portion in the air channel; and
a mount configured to mount the housing to an extruder head of an additive manufacturing device, and
a processor configured to:
supply power to the plurality of thin film gas sensors to bias the sensors;
receive output from each of the plurality of thin film gas sensors;
determine whether there is an abnormality in an additive manufacturing process manufacturing a product from one or more materials or composite material based on one or more combinations of the output from each of the plurality of thin film gas sensors during the additive manufacturing process and from a deployed machine learning model; and
generate a report for the additive manufacturing process containing the abnormality determination, wherein the received the output from each of the plurality of thin film gas sensors is in response to heating materials or composite materials at different temperatures, one of the materials or composite materials at a time and wherein the processor is configured to:
generate randomly a first dataset for training and a second dataset for testing a plurality of models using the received output;
train and test the plurality of models using one or more combinations of the output from each of the plurality of thin film gas sensors, the plurality of models is generated using a plurality of different machine learning techniques, the training based on the first dataset and the testing based on the second dataset; and
evaluate a prediction accuracy of each of the plurality of models using an
evaluation parameter and select a model from among the plurality of models to deploy as the deployed machine learning model for detecting the abnormality in the additive manufacturing process based on a comparison of the evaluation parameter for each of the plurality of models.

3. The additive manufacturing system of claim 2, wherein the first dataset and the second dataset further comprising data received from at least one different modality including different spectroscopy and mechanical analysis.

4. The additive manufacturing system of claim 3, wherein the different spectroscopy comprises at least one of mass spectroscopy, Raman spectroscopy and fourier transform infrared spectroscopy.

5. The additive manufacturing system of claim 3, wherein the data received from the at least one different modality is received substantially at the same time with the output from each of the plurality of thin film gas sensors.

6. The additive manufacturing system of claim 3, wherein the mechanical analysis comprises determining key locations within the product.

7. The additive manufacturing system of claim 6, wherein the processor is further configured to determine whether the abnormality occurred at one of the key locations and cause a stoppage in the additive manufacturing process of the product when the abnormality occurred at one of the key locations.

8. The additive manufacturing system of claim 1, wherein the abnormality is based on a predicted decomposition level determined from the output and from the deployed machine learning model.

9. The additive manufacturing system of claim 1, wherein at least one of the first electronic nose or the second electronic nose further comprises a communication interface, wherein the processor is further configured to receive printing conditions via the communication interface and a location of printing, wherein the printing conditions comprising an identifier of the one or more materials or composite materials used in the additive manufacturing process and a target temperature.

10. The additive manufacturing system of claim 9, wherein the processor is further configured to select the deployed machine learning model based on the identifier of the one or more materials or composite materials.

11. The additive manufacturing system of claim 9, wherein the processor is further configured to transmit the report via the communication interface.

12. The additive manufacturing system of claim 9, wherein the processor is further configured to determine a location of the printing based on the received location and configured to determine whether the location of the printing is at a key location and cause a stoppage in the additive manufacturing process of the product when an abnormality has occurred and the location of the printing is at the key location.

13. The additive manufacturing system of claim 1, wherein at least one of the first electronic nose or the second electronic nose comprises the processor.

14. The additive manufacturing system of claim 2, wherein a hotplate is used to control the temperatures of the materials or composite materials to obtain the first dataset and the second dataset.

15. The additive manufacturing system of claim 1, further comprising a first fan and a second fan respectively configured to move air toward the plurality of thin film gas sensors.

16. The additive manufacturing system of claim 1, further comprising a pipe forming each of the air channels, respectively.

17. The additive manufacturing system of claim 1, wherein the air channel comprising a plurality of openings, wherein the active sensor portion of each of the thin film gas sensors is connected to a circuit board, respectively, via a respective one of the openings.

18. The additive manufacturing system of claim 1, wherein the plurality of thin film gas sensors is positioned with the air channel based on operating temperature.

\* \* \* \* \*